United States Patent [19]

Saikawa et al.

[11] 4,395,412
[45] * Jul. 26, 1983

[54] 7α-METHOXYCEPHALOSPORINS

[75] Inventors: Isamu Saikawa; Shuntaro Takano; Hiroyuki Imaizumi; Isamu Takakura; Hirokazu Ochiai; Takashi Yasuda; Hideo Taki; Masaru Tai; Yutaka Kodama, all of Toyama, Japan

[73] Assignee: Toyama Chemical Co., Ltd., Tokyo, Japan

[*] Notice: The portion of the term of this patent subsequent to Dec. 12, 1995, has been disclaimed.

[21] Appl. No.: 221,622

[22] Filed: Dec. 31, 1980

Related U.S. Application Data

[60] Division of Ser. No. 117,784, Feb. 1, 1980, Pat. No. 4,321,265, which is a continuation of Ser. No. 926,939, Jul. 21, 1978, abandoned.

[30] Foreign Application Priority Data

Jul. 23, 1977 [JP] Japan .................................. 52-88733
Feb. 2, 1978 [JP] Japan .................................. 53-9869
Jun. 13, 1978 [JP] Japan .................................. 53-70417

[51] Int. Cl.³ .................. C07D 501/57; A61K 31/545
[52] U.S. Cl. ..................................... 424/246; 544/21; 544/26; 544/27
[58] Field of Search .................. 544/21, 16, 27, 28, 544/30; 424/246

[56] References Cited

U.S. PATENT DOCUMENTS 4,129,730 12/1978 Saikawa et al. ................... 544/21
4,263,292  4/1981 Saikawa et al. ................... 544/21
4,343,937  8/1982 Christensen et al. .............. 544/21

Primary Examiner—Nicholas S. Rizzo
Attorney, Agent, or Firm—Oblon, Fisher, Spivak, McClelland & Maier

[57] ABSTRACT

A 7α-methoxycephalosporin represented by the general formula:

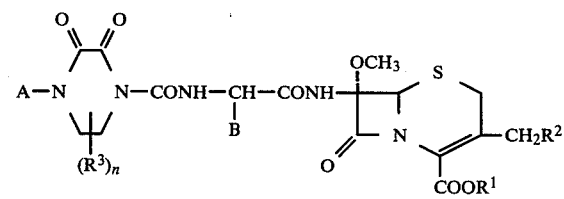

wherein $R^1$ represents a hydrogen atom or a carboxyl-protecting group; $R^2$ represents an organic group linked to the carbon atom through an oxygen or sulfur atom; $R^3$ represents a lower alkyl group; n is 0, 1 or 2; A represents a hydrogen atom or a substituted or unsubstituted alkyl group; and B represents a substituted or unsubstituted alkyl, cycloalkyl, cycloalkenyl, cycloalkadienyl or heterocyclic group, and a salt thereof. These compounds have a broad antibacterial spectrum, high resistance to β-lactamase produced from bacteria, and an effective antibacterial activity against clinical isolates of bacteria.

23 Claims, No Drawings

7α-METHOXYCEPHALOSPORINS

This is a division of application Ser. No. 117,784, filed Feb. 1, 1980 now U.S. Pat. No. 4,321,265 which is a continuation application of Ser. No. 926,939, filed July 21, 1978 abandoned.

This invention relates to novel 7α-methoxycephalosporins and methods for producing these compounds.

The compounds of this invention are characterized by having a broad antibacterial spectrum against Gram-positive and -negative bacteria, particularly having an excellent antibacterial activity against *Pseudomonas aeruginosa, Klebsiella pneumoniae* and Proteus species which have been known as causes for clinically serious infectious diseases, and being stable to β-lactamase produced from bacteria. They are, therefore, very useful in treating various infectious diseases.

Although conventional 7α-methoxycephalosporins are known to have an antibacterial activity against Gram-positive bacteria, they have defects of not exhibiting an effective antibacterial activity against *Pseudomonas aeruginosa, Klebsiella pneumoniae* and Proteus species which causes clinically serious infectious diseases and of being unstable to β-lactamase.

The present inventors have conducted extensive research on 7α-methoxycephalosporins which have no such defects as mentioned above. As a result, it has been found that novel compounds represented by the general formula (I), described hereinafter, in which the cephem ring bears an organic-group-substituted oxy- or thiomethyl group at the 3-position and a methoxy group at the 7α-position, and the amino group at the 7β-position is linked to the group

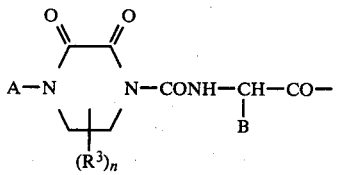

wherein $R^3$, n, A and B have the meanings described hereinafter, and salts of the compounds have none of the abovementioned defects.

It is an object of this invention to provide novel 7α-methoxycephalosporins having in their molecule a 2,3-dioxo-1-piperazinecarbonylamido group and a group B.

It is another object of this invention to provide novel 7α-methoxycephalosporins having a broad antibacterial spectrum.

It is a further object of the invention to provide novel 7α-methoxycephalosporins having high resistance to β-lactamase produced from bacteria.

It is a still further object of the invention to provide novel 7α-methoxycephalosporins having an effective antibacterial activity against clinical isolates of bacteria.

It is a still further object of the invention to provide a process for producing the novel 7α-methoxycepharosporins.

It is a still further object of the invention to provide a pharmaceutical composition containing the novel 7α-methoxycephalosporin or its salt as active ingredient.

Other objects and advantages of this invention will become apparent from the following description.

The compound of the present invention includes a 7α-methoxycephalosporin represented by the general formula:

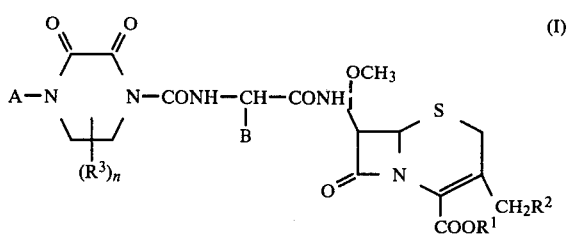

wherein $R^1$ represents a hydrogen atom or a carboxyl-protecting group; $R^2$ represents an organic group linked through an oxygen or sulfur atom; $R^3$ represents a lower alkyl group; n is 0, 1 or 2; A represents a hydrogen atom or a substituted or unsubstituted alkyl group; and B represents a substituted or unsubstituted alkyl, cycloalkyl, cycloalkenyl, cycloalkadienyl or heterocyclic group, and salts thereof.

The term "alkyl" used herein means a straight or branched chain alkyl having 1 to 14 carbon atoms, such as methyl, ethyl, propyl, isopropyl, butyl, pentyl, hexyl, heptyl, octyl, dodecyl or the like; the term "alkoxy" used herein means a monovalent -O-alkyl in which the alkyl defined above is bonded to oxygen, namely a straight or branched chain alkoxy having 1 to 14 carbon atoms; the term "lower alkyl" used herein means a straight chain alkyl having 1 to 5 carbon atoms, such as methyl, ethyl, propyl, butyl or pentyl; the term "lower alkoxy" used herein means a monovalent -O-lower alkyl in which the lower alkyl defined above is bonded to oxygen, namely a straight chain alkoxy having 1 to 5 carbon atoms; the term "acyl" used herein means an acyl having 1 to 10 carbon atoms, such as acetyl, propionyl, butyryl, benzoyl, naphthoyl, pentanecarbonyl, cyclohexanecarbonyl, furoyl, thenoyl or the like; and the term "acyloxy" used herein means a monovalent -O-acyl in which the acyl defined above is bonded to oxygen, namely an acyloxy having 1 to 10 carbon atoms. When the terms "acyl" and "acyloxy" means those formed from a heterocyclic ring containing N, O and/or S in any number in any position of the ring, the hetero atom or atoms are calculated as the number of carbon atoms.

In the general formulas described herein, $R^1$ is a hydrogen atom or a carboxyl-protecting group. The carboxyl-protecting groups in this invention are those which have conventionally been used in the penicillin and cephalosporin fields and include ester-forming groups which can be removed by catalytic reduction, chemical reduction or other treatments under mild conditions; ester-forming groups which can easily be removed in living bodies; and other known ester-forming groups which can easily be removed by treatment with water or an alcohol, such as organic silyl groups, organic phosphorus-containing groups, organic tin-containing groups, or the like.

Examples of suitable carboxyl-protecting groups are:
(a) Alkyl groups;
(b) Substituted lower alkyl groups, at least one of the substituents of which is chloro, bromo, fluoro, nitro, carboalkoxy, acyl, lower alkoxy, oxo, cyano, lower alkylthio, lower alkylsulfinyl, lower alkylsulfonyl, lower alkoxycarbonyl, 1-indanyl, 2-indanyl, furyl, pyridyl, 4-imidazolyl, phthalimido, acetidino, aziridino, pyrrolidinyl, piperidino, morpholino, thiomorpholino, N-lower-alkylpiperazino, 2,5-dimethylpyrrolidinyl, 1,4,5,6-tetrahydropyrimidinyl, 4-methylpiperidino, 2,6-dimethylpiperidino, lower alkylamino, di-lower-alkylamino, acyloxy, acylamino, di-lower-alkylaminocarbonyl, lower alkoxycarbonylamino, lower alkoxycarbonyloxy, or lower alkylanilino or lower alkylanilino substituted by chloro, bromo, lower alkyl, or lower alkoxy;

(c) Cycloalkyl groups containing 3 to 7 carbon atoms, lower-alkyl-substituted $C_{3-7}$ cycloalkyl groups, or (2,2-di(lower alkyl)-1,3-dioxolan-4-yl)methyl groups;

(d) Alkenyl groups containing up to 10 carbon atoms;

(e) Alkinyl groups containing up to 10 carbon atoms;

(f) Phenyl group, substituted phenyl groups, at least one of the substituents of which is one selected from the substituents examplified in above (b); or aryl groups represented by the formula:

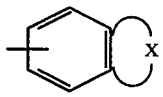

wherein X is —CH=CH—O—, —CH=CH—S—, —CH$_2$CH$_2$S—, —CH=N—CH=N—, —CH=CH—CH=CH—, —CO—CH=CH—CO—, or —CO—CO—CH=CH—, or substituted derivatives thereof, the substituents of which are ones selected from those exemplified in above (b), or the formula:

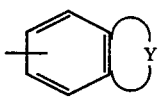

wherein Y is a lower alkylene group such as —(CH$_2$)$_3$— and —(CH$_2$)$_4$—, or substituted derivatives thereof, the substituents of which are ones selected from those exemplified in above (b);

(g) Aralkyl groups such as benzyl group or substituted benzyl groups, at least one of the substituents of which is one selected from those exemplified in above (b);

(h) Heterocyclic groups such as furyl, quinolyl, methyl-substituted quinolyl, phenazinyl, 1,3-benzodioxolanyl, 3-(2-methyl-4-pyrrolinyl), 3-(4-pyrrolinyl) and N-(methylpyridyl), or substituted heterocyclic groups, at least one of the substituents of which is one selected from those exemplified in above (b);

(i) Alicyclic indanyl or phthalidyl groups or substituted derivatives thereof, the substituent of which is methyl, chloro, bromo or fluoro; alicyclic tetrahydronaphthyl group or its substituted derivative, the substituent of which is methyl, chloro, bromo or fluoro, trityl group, cholesteryl group, and bicyclo(4,4,0)-decyl group.

The carboxyl-protecting groups listed above are typical examples, and there may be used any groups selected from those disclosed in U.S. Pat. Nos. 3,499,909; 3,573,296; and 3,641,018, West German Offenlegungsschrift Nos. 2,301,014; 2,253,287; and 2,337,105.

$R^2$ in the general formulas is "an organic group linked through an oxygen or sulfur atom". Examples of $R^2$ are lower alkoxy groups; lower alkylthio groups; acyloxy groups; carbamoyloxy group; and heterocyclic thio groups containing O, S and N alone or in any combination in any position, such as oxazolylthio, thiazolylthio, isoxazolylthio, isothiazolylthio, imidazolylthio, pyrazolylthio, pyridylthio, pyrazinylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzthiazolylthio, triazolopyridylthio, purinylthio, pyridine-1-oxide-2-ylthio, and the like.

Further, the above-mentioned $R^2$ groups may be substituted by a halogen atom or a lower alkyl, phenyl, $C_{2-5}$ alkenyl, hydroxyl, lower alkoxy, lower alkylthio, nitro, cyano, lower alkylamino, di-lower-alkylamino, acylamino, acyl, acyloxy, acyl-lower alkyl, carboxyl, carbamoyl, amino-lower alkyl, N-lower-alkylamino-lower-alkyl, N,N-di-lower-alkylamino-lower-alkyl, hydroxy-lower-alkyl, hydroxyimino-lower-alkyl, lower-alkoxy-lower-alkyl, carboxy-lower-alkyl, sulfo-lower-alkyl, sulfo, sulfamoyl-lower-alkyl, sulfamoyl, carbamoyl-lower-alkyl, carbamoyl-$C_{2-5}$ alkenyl, N-hydroxycarbamoyl-lower-alkyl or the like.

A in the general formulas is a hydrogen atom or a substituted or unsubstituted alkyl group. Examples of the said alkyl group are as exemplified in the definition of alkyl hereinbefore. Examples of substituents of the substituted alkyl groups for group A include halogen atoms, lower alkoxy groups, cyano group, nitro group, carboxyl group, lower alkoxycarbonyl groups, hydroxyl group, lower alkylthio groups, acyl groups, N,N-disubstituted amino groups, and the like. B in the general formulas is a substituted or unsubstituted alkyl, cycloalkyl, cycloalkenyl, cycloalkadienyl or heterocyclic group. Examples of the said alkyl group are as exemplified in the definition of alkyl hereinbefore. Examples of the cycloalkyl group are cyclopentyl, cyclohexyl and the like. The cycloalkenyl group includes for example, cyclopentenyl, cyclohexenyl and the like. Examples of the cycloalkadienyl group are cyclopentadienyl, cyclohexadienyl, and the like. The heterocyclic groups are those groups containing S, O and N alone or in any combination in any position, such as furyl, thienyl, oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, 1,3,4-oxadiazolyl, 1,2,4-oxadiazolyl, 1,3,4-thiadiazolyl, 1,2,4-thiadiazolyl and the like.

Each group represented by B includes position isomers (for example, the thienyl group includes 2-thienyl and 3-thienyl). The substituents borne by the groups represented by B include halogen atoms, lower alkyl groups, lower alkoxy groups, hydroxyl group, acyl groups, acyloxy groups, mercapto group, lower alkylthio groups, nitro group, amino group, protected amino groups, imino group, protected imino groups, carboxyl group and the like.

The protecting groups of the above-mentioned protected amino and imino groups include all groups which can usually be used as amino-protected groups, such as easily removable groups such as, for example, trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tert.-butoxycarbonyl, p-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-yl-methoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like; and other easily removable amino-protecting groups, for example, trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-(N-(2-methoxyphenyl)carbamoyl)-2-propylidene, 1-(N-(4-methoxyphenyl)carbamoyl)-2-propylidene, 2-ethoxycarbonylcyclohexylidene, 2-ethoxycarbonylcyclopentylidene, 2-acetylcyclohexylidene, 3,3-dimethyl-5-oxocyclohexylidene, di- or tri-alkylsilyl, and the like.

When tautomerism is known to exist in any of the groups represented by B, the tautomers are included in the scope of this invention. For instance, 2-(substituted-)aminothiazolyl group exists in tautomeric forms which are in equilibrium as shown by the following equilibrium formulas:

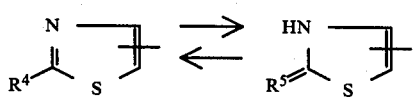

wherein $R^4$ represents an amino or a protected amino group and $R^5$ represents an imino or a protected imino group.

The salt of the 7α-methoxycephalosporin of this invention represented by the general formula (I) includes those formed at the acidic group and those formed at the basic group, which are well known in the penicillin and cephalosporin fields. Of the salts, pharmaceutically acceptable salts are preferred. The salts formed at the acidic group include salts with alkali metals such as sodium, potassium and the like; alkaline earth metals such as calcium, magnesium and the like; ammonium; and nitrogen-containing organic bases such as procaine, dibenzylamine, N-benzyl-β-phenethylamine, 1-ephenamine, N,N-dibenzylethylenediamine, trimethylamine, triethylamine, tributylamine, pyridine, dimethylaniline, N-methylpiperidine, N-methylmorpholine, diethylamine, and dicyclohexylamine.

The salts formed at the basic group include salts with mineral acids such as hydrochloric acid, sulfuric acid and the like; organic carboxylic acids such as oxalic acid, formic acid, trichloroacetic acid, trifluoroacetic acid and the like; and organic sulfonic acids such as methanesulfonic acid, toluenesulfonic acid, naphthalenesulfonic acid, and the like.

All optical isomers and racemic compounds, and all crystal forms and hydrates of the 7α-methoxycephalosporin represented by the general formula (I) and salt thereof are included within the scope of this invention.

The compounds represented by the general formula (I) or salts thereof are produced by the known methods such as, for example, those described below.

Production method (1): A method by which a compound of the general formula (II):

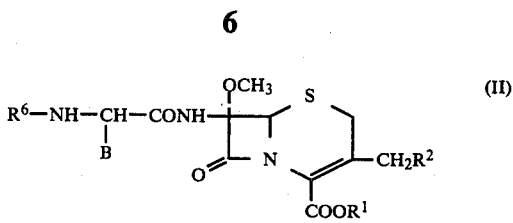

wherein $R^6$ represents a hydrogen atom, an organic silyl group or organic phosphorus-containing group; and $R^1$, $R^2$ and B have the same meanings as defined above, is reacted with a reactive derivative in the carboxyl group of a compound represented by the general formula (III):

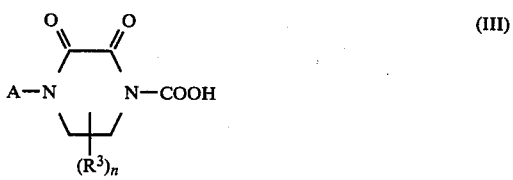

wherein $R^3$, n and A have the same meanings as defined above.

Production method (2): A method by which a compound of the general formula (IV):

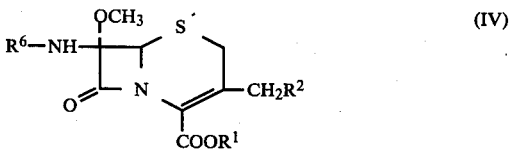

wherein $R^1$, $R^2$ and $R^6$ have the same meanings as defined above, is reacted with a compound represented by the general formula (V):

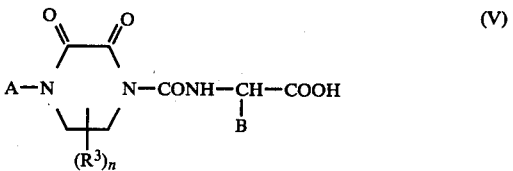

wherein $R^3$, n, A and B have the same meanings as defined above or a reactive derivative in the carboxyl group of said compound (V).

Production method (3): A method by which a cephalosporin of the general formula (VI):

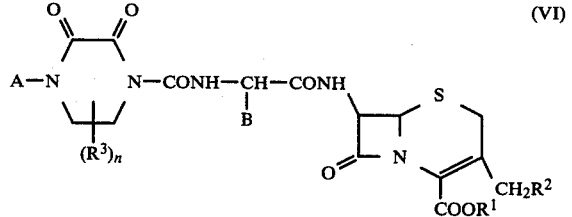

wherein $R^1$, $R^2$, $R^3$, n, A and B have the same meanings as defined above, is reacted, in the presence of methanol, with an alkali metal methylate represented by the general formula (VII):

$M^{1+} \; {}^-OCH_3$ (VII)

wherein $M^1$ represents an alkali metal and then reacted with a halogenating agent.

Production method (4): A method by which a 7α-methoxycephalosporin of the general formula (VIII):

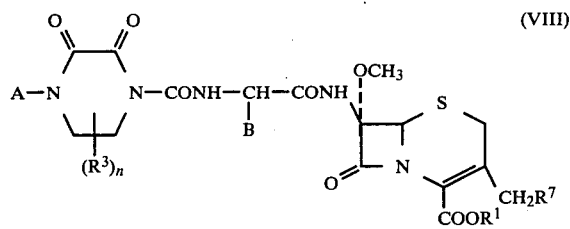

wherein $R^7$ represents a group easily replaced by a nucleophilic reagent; and $R^1$, $R^3$, n, A and B have the same meanings as defined above, is reacted with a compound represented by the general formula (IX):

$R^2 M^2$ (IX)

wherein $M^2$ represents a hydrogen atom, an alkali metal or an alkaline earth metal; and $R^2$ has the same meaning as defined above.

The organic silyl groups and the organic phosphorus-containing groups represented by $R^6$ in the above-mentioned general formulas include those groups which are conventionally used as amino- or carboxyl-protecting group in the penicillin and cephalosporin synthesis fields, such as

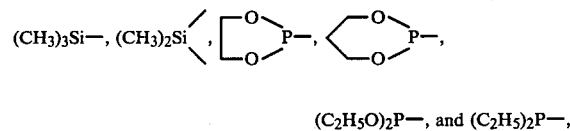

$(C_2H_5O)_2P-$, and $(C_2H_5)_2P-$, which are easily removed by treatment wity, for example, water or an alcohol.

The groups represented by $R^7$, which are easily replaceable by a nucleophilic reagent, include halogen atoms such as chlorine, bromine and the like; lower alkanoyloxy groups such as formyloxy, acetoxy, propionyloxy, butyryloxy, pivaloyloxy and the like; arylcarbonyloxy groups such as benzoyloxy, naphthoyloxy and the like; arylthiocarbonyloxy groups such as thiobenzoyloxy, thionaphthoyloxy and the like; arylcarbonylthio groups such as benzoylthio, naphthoylthio and the like; arylthiocarbonylthio groups such as thiobenzoylthio, thionaphthoylthio and the like; carbamoyloxy group; thiocarbamoyloxy group; pyridine-N-oxide-2-yl group; and pyridazine-N-oxide-6-yl group. These groups represented by $R^7$ may further contain substituents such as, for example, a halogen atom, nitro group, lower alkyl group, lower alkoxy group, lower alkylthio group, acyl group and the like.

The compound represented by the general formula (V) is easily obtained by the reaction between an alkali metal salt, an alkaline earth metal salt or an organic base salt of a compound represented by the general formula (X):

$$H_2N-\underset{B}{CH}-COOH \quad (X)$$

wherein B has the same meaning as defined above, and a reactive derivative in the carboxyl group of a compound represented by the general formula (III) in the presence of an acid-binding agent in an inert solvent.

The compounds represented by the general formulas (II) and (IV) may be synthesized in a manner known per se, for example, the manner described in the Journal of Synthetic Organic Chemistry, Japan, Vol. 35, 568–574 (1977).

The modes of practice of the production methods (1), (2), (3) and (4) are described below.

The methods (1) and (2) can be carried out under nearly the same conditions. The compound (II) or (IV) is dissolved or suspended in an inert solvent such as, for example, water, acetone, tetrahydrofuran, dioxane, acetonitrile, dimethylformamide, dimethylacetamide, methanol, ethanol, methoxyethanol, diethyl ether, diisopropyl ether, benzene, toluene, methylene chloride, chloroform, ethyl acetate, or methyl isobutyl ketone, each alone or in admixture of two or more. To the resulting solution or suspension is added a reactive derivative in the carboxyl group of the compound (III), or the compound (V) or a reactive derivative in the carboxyl group or the compound (V). The mixture is allowed to react in the presence or absence of a base at $-60°$ to $80°$ C., preferably $-40°$ to $30°$ C. A reaction time of 5 minutes to 5 hours is generally sufficient.

The bases used in the above reaction include inorganic bases such as alkali metal hydroxides, alkali metal hydrogen carbonates, alkali metal carbonates and alkali metal acetates; tertiary amines such as trimethylamine, triethylamine, tributylamine, pyridine, N-methylpiperidine, N-methylmorpholine, lutidine, collidine and the like; and secondary amines such as dicyclohexylamine, diethylamine and the like.

When the compound (V) or a salt thereof is used in the method (B 2) as the starting material, the reaction can be carried out in the presence of a dehydrating-condensing agent such as, for example, N,N'-dicyclohexylcarbodiimide, N-cyclohexyl-N'-morpholinoethylcarbodiimide, N,N'-diethylcarbodiimide, N,N'-carbonyl bis(2-methylimidazole), trialkyl phosphites, ethyl polyphosphate, phosphorus oxychloride, phosphorus trichloride, 2-chloro-1,3,2-dioxaphospholane, oxazolyl chloride, dimethylchloroforminium chloride, and dimethylethoxyforminium chloride.

The method (3) is carried out in the following way: A cephalosporin of the formula (VI) obtained in a known manner (Japanese Patent Application Kokai (Laid-Open) Nos. 70,788/76 and 113,890/76) is dissolved or suspended in an inert solvent such as, for example, tetrahydrofuran, dioxane, ethylene glycol dimethyl ether, methylene chloride, chloroform, dimethylformamide, dimethylacetamide, acetonitrile, methanol or the like or a mixture of two or more of these solvents. To the resulting solution or suspension is added an alkali metal methylate (VII) together with methanol. The resulting mixture is subjected to reaction, and the reaction mixture is then reacted with a halogenating agent. In this reaction, methanol is used in excess and the amount of the alkali metal methylate (VII) used is preferably 2 to 6 equivalents per equivalent of the cephalosporin (VI) used. The term "in excess" means an amount of more than 1 equivalent per equivalent of the cephalosporin (VI). All of the above reactions are carried out at −120° to −10° C., preferably −100° to −50° C. A reaction time of 5 to 30 minutes is sufficient and the reaction is terminated by acidifying the reaction system.

The halogenating agent used in this method is generally known to be a source for supplying a positive halogen atom such as Cl+, Br+ or I+. Examples of such halogenating agents include halogens such as chlorine, bromine and the like; N-haloimides such as N-chlorosuccinimide, N-bromosuccinimide and the like; N-haloamides such as N-chloroacetamide, N-bromoacetamide and the like; N-halosulfonamides such as N-chlorobenzenesulfonamide, N-chloro-p-toluenesulfonamide and the like; 1-halobenzotriazoles; 1-halotriazines; organic hypohalogenite such as tert.-butyl hypochlorite, tert.-butyl hypoiodide and the like; halohydantoins such as N,N-dibromohydantoin, and the like. Of these halogenating agents, tert.-butyl hypochlorite is preferred. The halogenating agent is used in an amount sufficient for supplying a positive halogen in an amount equivalent to that of the cephalosporin of the general formula (VI).

Suitable acids for the termination of reaction are those which, when added to a cold reaction mixture, will not cause solidification of the reaction mixture or freezing of the reaction mixture into a heavy viscous mixture. Examples of the suitable acids are 98% formic acid, glacial acetic acid, trichloroacetic acid and methanesulfonic acid.

After the termination of the reaction, the excess halogenating agent can be removed by treating with a reducing agent such as trialkyl phosphite, sodium thiosulfate, or the like.

In carrying out the production method (4), when a compound of the formula (VIII) is used other than the compound in which the group $R^7$ is a heterocyclic aromatic amine-N-oxide thio group having a thio group on the carbon atom adjacent to the N-oxide group, said compound is reacted with a compound of the formula (IX) in an inert solvent such as, for example, water, methanol, ethanol, propanol, isopropanol, butanol, acetone, methyl ethyl ketone, methyl isobutyl ketone, tetrahydrofuran, dioxane, acetonitrile, ethyl acetate, 2-methoxyethanol, dimethoxyethane, dimethylformamide, dimethyl sulfoxide, dimethylacetamide, dichloroethane, chloroform, dichloromethane, and the like, alone or in admixture of two or more.

The above reaction is carried out preferably in a strongly polar solvent such as water. It is advantageous to maintain the pH of the reaction solvent at 2 to 10, preferably 4 to 8. The reaction is effected after the addition of a buffer such as sodium phosphate to adjust the pH to a desired value. Although the reaction conditions are not critical, the reaction is generally carried out at 0° to 100° C. for several hours to several tens of hours.

When a compound of the general formula (VIII) in which the group $R^7$ is a heterocyclic aromatic amine-N-oxide thio group having a thio group on the carbon atom adjacent to the N-oxide group is used, the compound of the general formula (VIII) and a compound of the general formula (IX) are reacted with each other in the inert solvent listed above in the presence of a divalent copper compound. This procedure is particularly useful when the compound of the general formula (IX) is an alcohol such as methyl alcohol, ethyl alcohol, propyl alcohol, isopropyl alcohol, n-butyl alcohol, benzyl alcohol, ethylene glycol or the like. In this case, the reaction proceeds smoothly by the use of an excess of the alcohol to serve as a solvent. The divalent copper compounds used in this procedure are inorganic or organic divalent copper compounds such as, for example, cupric chloride, cupric bromide, cupric fluoride, cupric nitrate, cupric sulfate, cupric borate, cupric phosphate, cupric cyanide, cupric formate, cupric acetate, cupric propionate, cupric citrate, cupric tartarate, cupric benzoate, and cupric salicylate. The amount of the divalent copper compound used is preferably 0.5 mole or more per mole of the compound represented by the general formula (VIII). Although depending on the types of the compound of the general formula (VIII), divalent copper compound, and compound of the general formula (IX) used, generally the reaction temperature is 0° to 100° C., and the reaction time is several minutes to several days.

Conversion from a compound of the general formula (I) in which $R^1$ is a carboxyl-protecting group to a compound of the general formula (I) in which $R^1$ is a hydrogen atom or a salt of the latter compound, conversion from a compound of the general formula (I) in which $R^1$ is a hydrogen atom to a salt or to a compound of the general formula (I) in which $R^1$ is a carboxyl-protecting group, or conversion from a salt of a compound of the general formula (I) to its free acid can be carried out in a conventional manner.

In reacting a compound in which the group A, B or $R^2$ is reactive, the reactive group can be protected with a protecting group usually used in protecting a carboxyl, amino or hydroxyl group. After the reaction, such a protecting group can be removed in a conventional manner to regenerate the group A, B or $R^2$.

The conditions for the production are not limited to those described above, but suitably modified in accordance with the particular type of reagent used.

Isolation of a 7α-methoxycephalosporin (I) or a salt thereof from the reaction mixture can be carried out in a conventional manner.

The method for the production of a 7α-methoxycephalosporin represented by the general formula (I) and a salt thereof is not limited to those described above. These compounds can be produced also by other known methods.

The 7α-methoxycephalosporin represented by the general formula (I) and the salt thereof thus obtained are very useful for the therapy of human and animal diseases because of their broad antibacterial spectrum against Gram-positive bacteria and Gram-negative bacteria, their excellent antibacterial activity to *Pseudomonas aeruginosa, Klebsiella pneumoniae* and *Protius* species, and their stability to β-lactamase.

Among various 7α-methoxycephalosporins according to this invention, those represented by the following formula (Ia) and salts thereof are preferred:

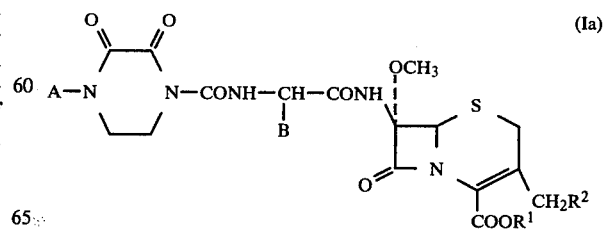

wherein A represents a hydrogen atom or a lower alkyl group; B represents a thienyl group, a furyl group,

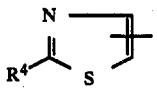

or its tautomer

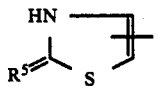

(R⁴ represents an amino group or a protected amino group and R⁵ represents an imino group or a protected imino group), a $C_{1-4}$-alkyl group, or 1,4-cyclohexadienyl group; and $R^1$ and $R^2$ have the same meanings as defined above. Of the 7α-methoxycephalosporin represented by the above formula (Ia) and salt thereof, most preferred are those in which B is a thienyl group, a furyl group,

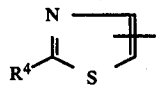

or its tautomer

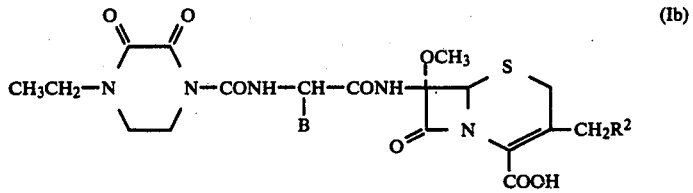

($R^4$ and $R^5$ have the saie meanings as defined above), particularly those in which $R^2$ is an acetoxy group, substituted 5-(1,2,3,4-tetrazolyl)thio group or 2-(1,3,4-thiadiazolyl)thio group.

Antibacterial activities of the representative compounds (Ib) of the 7α-methoxycephalosporins according to this invention are shown in Table 1.

The figures given in Table 1 represent the minimum inhibitory concentration (MIC in mcg/ml) of each compound, which was determined according to the method described in "Chemotherapy (Society of Chemotherapy, Japan), Vol. 16, 98–99 (1968)": A culture obtained by cultivating the test bacterium in a Heart Infusion broth (Eiken Kagaku Co.) was inoculated into a Heart Infusion agar medium (Eiken Kagaku Co.). After 20 hours of the incubation at 37° C., the growth of the bacterium was inspected to determin the minimum inhibitory concentration (MIC in mcg/ml). The inoculation rate of the bacterium was $10^4$ cells/plate ($10^6$ cells/ml).

(1) Minimum inhibitory concentration (MIC in mcg/ml).

TABLE 1

Compound (Ib): B = thiophene-2-yl (2-thienyl), with $-S-$ linked triazole bearing $R^2$

| Bacteria | CS-1170 (Control) | $R^2$ = $CH_3$ | $CH_2CH_2N(CH_3)_2$ | $CH_2COOH$ | $-OCOCH_3$ | $CH_2CONH_2$ | $CH_2CH_2OH$ | $-CH_2CH_2N(CH_3)_2$ (N-substituted) |
|---|---|---|---|---|---|---|---|---|
| | | 3.13 | 6.25 | 6.25 | 6.25 | 3.13 | 3.13 | 6.25 |
| S. aureus F-19 (Penicillinase-producing bacterium) | 1.56 | | | | | | | |
| E. coli NIHJ | 0.39 | ≦0.1 | ≦0.1 | ≦0.1 | ≦0.1 | ≦0.1 | ≦0.1 | ≦0.1 |
| K. pneumoniae Y-50 | 0.39 | 0.39 | 0.78 | 6.25 | 1.56 | 0.39 | 0.39 | 0.78 |
| Prot. vulgaris GN-76 | 3.13 | 0.2 | | 0.78 | 1.56 | 0.78 | 0.39 | 3.13 |
| Ps. aeruginosa IFO-3445 | ≧200 | 12.5 | | 25 | 50 | 12.5 | 12.5 | 50 |
| Ser. marcescens W-8 | ≧200 | 25 | | 50 | 100 | 25 | 50 | 50 |
| Acinetobacter caloaceticus A-6 | 50 | 12.5 | | 25 | 25 | 6.25 | 6.25 | 25 |
| C. freundii GN-346 (Cephalosporinase-producing bacterium) | ≧200 | 25 | | 50 | 100 | | 12.5 | 25 |
| Ent. cloacae IID977 | ≧200 | 25 | | 25 | 50 | 12.5 | 25 | 25 |
| Citrobacter N-7 | 25 | 0.78 | | 1.56 | 3.13 | 3.13 | 1.56 | 3.13 |
| Ser. marcescens IID620 | 3.13 | 0.78 | | 0.78 | 3.13 | 0.2 | 0.2 | 0.2 |
| Klebsiella spp. Y-72 | 12.5 | 6.25 | | 25 | 6.25 | 1.56 | 1.56 | |
| Ser. marcescens W-35 | 100 | 6.25 | | 100 | 50 | 12.5 | 12.5 | |
| Ps. aeruginosa S-68 | ≧200 | 12.5 | | 50 | 50 | 12.5 | 12.5 | |

Compound (Ib) continued: B = thiophene-2-yl

| Bacteria | CS-1170 (Control) | $R^2$ = $CH_2CH_2N(CH_3)_2$ | $CH_2COOH$ (S-linked) | $CH=CH_2$ | $CH_2CH_2NH_2$ | $CF_2C=NOH$ / $CH_3$ | $CH_2COCH_3$ |
|---|---|---|---|---|---|---|---|
| | | 6.25 | 6.25 | 3.13 | 6.25 | 3.13 | 6.25 |
| S. aureus F-19 (Penicillinase-producing bacterium) | 1.56 | | | | | | |
| E. coli NIHJ | 0.39 | ≦0.1 | ≦0.1 | ≦0.1 | ≦0.1 | ≦0.1 | ≦0.1 |
| K. pneumoniae Y-50 | 0.39 | 0.78 | 0.39 | 0.39 | 0.78 | 0.78 | 0.39 |

TABLE 1-continued

| Bacteria | | | | | | | | | |
|---|---|---|---|---|---|---|---|---|---|
| Prot. vulgaris GN-76 | 3.13 | 1.56 | 0.78 | 0.78 | 0.78 | 0.78 | 0.78 | 0.78 | 0.78 |
| Ps. aeruginosa IFO-3445 | ≥200 | 50 | 25 | 25 | 25 | 12.5 | 25 | 25 | 25 |
| Ser. marcescens W-8 | ≥200 | 50 | 25 | 25 | 25 | 50 | 50 | 50 | 50 |
| Acinetobacter caloaceticus A-6 | 50 | 12.5 | 12.5 | 12.5 | 12.5 | 12.5 | 12.5 | 25 | 25 |
| C. freundii GN-346 (Cephalosporinase-producing bacterium) | ≥200 | 25 | 100 | 12.5 | | 25 | 50 | | |
| Ent. cloacae IID977 | ≥200 | 25 | 100 | 25 | | 50 | 25 | | 50 |
| Citrobacter N-7 | 25 | 6.25 | 12.5 | 3.13 | | 3.13 | 6.25 | | 6.25 |
| Ser. marcescens IID620 | 3.13 | 0.39 | 0.78 | 0.2 | | 0.2 | 0.2 | | 0.2 |
| Klebsiella spp. Y-72 | 12.5 | 12.5 | 1.56 | 6.25 | | 3.13 | 6.25 | 6.25 | 6.25 |
| Ser. marcescens W-35 | 100 | 50 | 12.5 | 12.5 | | 6.25 | 25 | 25 | 25 |
| Ps. aeruginosa S-68 | ≥200 | 25 | 25 | 12.5 | | 12.5 | 12.5 | 12.5 | 25 |

Compound (Ib)

| | | | B | | | | | | |
|---|---|---|---|---|---|---|---|---|---|

R² : (various substituents with thiadiazole/tetrazole/thiazole groups)

| Bacteria | CS-1170 (Control) | CH₂CONHOH (thiadiazole) | CH₃ (tetrazole, phenyl) | CH₃ | CH₂CONH₂ | CH₂CH₂OH | CH=CH₂ | (aminothiazole) | CH₃ |
|---|---|---|---|---|---|---|---|---|---|
| S. aureus F-19 (Penicillinase-producing bacterium) | 1.56 | 25 | 3.13 | 6.25 | 6.25 | 6.25 | 3.13 | 3.13 | |
| E. coli NIHJ | 0.39 | ≤0.1 | ≤0.1 | ≤0.1 | ≤0.1 | ≤0.1 | ≤0.1 | ≤0.1 | |
| K. pneumoniae Y-50 | 0.39 | 1.56 | 0.78 | 0.2 | 0.2 | 0.2 | 0.2 | 0.2 | |
| Prot. vulgaris GN-76 | 3.13 | 0.78 | 3.13 | 0.78 | 1.56 | 1.56 | 3.13 | 0.78 | |
| Ps. aeruginosa IFO-3445 | ≥200 | 12.5 | 12.5 | 12.5 | 12.5 | 12.5 | 25 | 12.5 | |
| Ser. marcescens W-8 | ≥200 | 100 | 100 | 100 | | | | 100 | |
| Acinetobacter caloaceticus A-6 | 50 | 1.56 | 6.25 | 12.5 | | | | 25 | |
| C. freundii GN-346 (Cephalosporinase-producing bacterium) | ≥200 | ≥200 | 25 | 25 | | | | 50 | |
| Ent. cloacae IID977 | ≥200 | 200 | 25 | 25 | 25 | 25 | 25 | 25 | |
| Citrobacter N-7 | 25 | 50 | 6.25 | 6.25 | | | | 1.56 | |
| Ser. marcescens IID620 | 3.13 | 0.78 | 0.78 | ≤0.1 | ≤0.1 | ≤0.1 | ≤0.1 | ≤0.1 | |
| Klebsiella spp. Y-72 | 12.5 | 100 | 12.5 | 6.25 | | | | 1.56 | |
| Ser. marcescens W-35 | 100 | 200 | 50 | 12.5 | | | | 6.25 | |
| Ps. aeruginosa S-68 | ≥200 | 25 | 25 | 25 | | | | 25 | |

Compound (Ib)

TABLE 1-continued

| | | B | | | |
|---|---|---|---|---|---|
| Bacteria | CS-1170 (Control) | R² -S-[triazole]-CH₂CONH₂ | —OCOCH₃ | -S-[thiadiazole]-NH₂ | -S-[thiadiazole]-CH₃ |
| S. aureus F-19 (Penicillinase-producing bacterium) | 1.56 | 3.13 | 6.25 | 6.25 | 6.25 |
| E. coli NIHJ | 0.39 | ≦0.1 | ≦0.1 | ≦0.1 | ≦0.1 |
| K. pneumoniae Y-50 | 0.39 | | | | |
| Prot. vulgaris GN-76 | 3.13 | 1.56 | 3.13 | 3.13 | 3.13 |
| Ps. aeruginosa IFO-3445 | ≧200 | 12.5 | 25 | | 25 |
| Ser. marcescens W-8 | ≧200 | | | | |
| Acinetobacter calcoaceticus A-6 | 50 | 12.5 | 25 | 25 | 25 |
| C. freundii GN-346 (Cephalosporinase-producing bacterium) | ≧200 | | | | |
| Ent. cloacae IID977 | ≧200 | | | | |
| Citrobacter N-7 | 25 | | | | |
| Ser. marcescens IID620 | 3.13 | ≦0.1 | 0.39 | 0.39 | 0.39 |
| Klebsiella spp. Y-72 | 12.5 | | | | |
| Ser. marcescens W-35 | 100 | | | | |
| Ps. aeruginosa S-68 | ≧200 | | | | |

Note: CS-1170 means

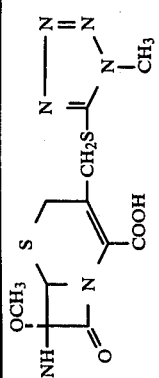

unit: mcg/ml (2) Stability to β-lactamase.

The stability to β-lactamase was examined by iodometry at 30° C. by the method of Perret (Perret, C. J., "Iodometric assay of penicillinase", Nature, 174, 1012–1013 (1954)), except that a 0.1 M phosphate buffer solution (pH 7.0) was used in place of the 0.2 M phosphate buffer solution (pH 6.5). The stability of each compound was shown in Table 2 in terms of relative degree of hydrolysis, assuming the stability of Cephaloridin (CER) to cephalosporinase as 100 and the stability of Penicillin G (PC-G) to penicillinase as 100.

TABLE 2

| | Stability to β-lactamase | | | | |
|---|---|---|---|---|---|
| Cephalosporinase- or penicillinase- producing bacteria | | PC-G | CER | CEZ | T-1414 |
| Cephalosporinase | E. coli GN-5482 | 22 | 100 | 130 | <0.1 |
| | S. marcescens W-8 | 21 | 100 | 94 | 0.02 |
| Penicillinase | E. coli TK-3 | 100 | 115 | 21 | <0.003 |
| | K. pneumoniae Y-4 | 100 | 41 | 4 | <0.09 |
| | P. aeruginosa GN-3379 | 100 | 18 | 2 | 0.03 |

Note:
CEZ means Cefazolin

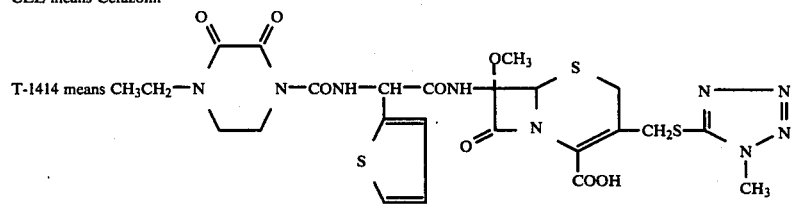

T-1414 means (3) Inhibitory does to β-lactamase.

The inhibitory does ($ID_{50}$) of T-1414 to β-lactamase was as shown in Table 3, as assayed by the iodometric method of Perret using Cefazolin as substrate.

TABLE 3

| Inhibitory dose to β-lactamase | |
|---|---|
| Cephalosporinase-producing bacteria | $ID_{50}$ (μg/ml) |
| E. coli GN-5482 | 0.82 |
| S. marcescens W-8 | 0.54 |
| C. freundii GN-346 | 1.7 |

(4) Infection-protective activity.

Four-week old ICR-strain mice (male) in groups, each group consisting of five mice, were inoculated intraperitoneally with a prescribed quantity of a pathogenic bacterium suspended in 5% mucin. After one hour from the inoculation, the mice were subcutaneously administered with the test preparation to determine the infection-protective activity. The results obtained were as shown in Table 4. The figures in Table 4 represent the protective activity in terms of $ED_{50}$.

TABLE 4

| | | Infection-protective activity | | | |
|---|---|---|---|---|---|
| | | MIC (mcg/ml) | | | |
| Strain | Challenge dose (cells/mouse) | Inoculated bacteria quantity (cells/ml) | T-1414 | CS-1170 | $ED_{50}$ (subcutaneous) (mg/mouse) T-1414 CS-1170 |
| S. marcescens W-35 | 2.5 × $10^5$ | $10^8$ | 12.5 | 200 | 0.84   15.1 |
| | | $10^6$ | 6.25 | 100 | |

Note:
CS-1170 is the same as defined in Table 1.
T-1414 is the same as defined in Table 2.

The 7α-methoxycephalosporins of this invention are lox-toxic. For instance, T-1414 showed a $LD_{50}$ of 5 g/kg or more (ICR-strain mice; intravenous).

The 7α-methoxycephalosporins of this invention represented by the general formula (I) and salts thereof are administered to man and animals in the form of free acid or pharmaceutically acceptable salt or ester. The compound is formulated into various dosage forms which are customary in penicillin or cephalosporin preparations such as, for example, capsules, syrups and injections and administered either orally or parenterally.

The invention is illustrated below in detail with reference to Examples which, however, are merely illustrative and not limitative. In the Examples, all percentages are by weight unless otherwise indicated.

EXAMPLE 1

(1) In a mixture of 20 ml of anhydrous chloroform and 5 ml of anhydrous tetrahydrofuran was dissolved 0.80 g of diphenylmethyl 7β-[D(−)-α-(4-ethyl-2,3-dioxo-1-piperazinecarboxamido)-α-(2-thienyl)-acetamido]-3-[5-(1-methyl-1,2,3,4-tetrazolyl)thiomethyl]-Δ³-cephem-4-carboxylate. The solution was cooled to −70° C. and, while maintaining the temperature at −70° C., to the solution was added 3.5 ml of a methanol solution of lithium methoxide (1.425 mmoles/ml). To the resulting mixture, after 3 minutes of stirring, was added 0.18 ml of tert.-butyl hypochlorite and stirred for 15 minutes at the same temperature, after which 0.29 ml of acetic acid and 0.1 ml of triethyl phosphite were added in this order. Thereafter, the temperature of the reaction system was elevated to room temperature. The reaction mixture was discharged into 25 ml of a citrate buffer solution (pH 7.0). The organic layer was separated, washed with water, dried over magnesium sulfate, and freed from the solvent by distillation under reduced pressure. The residue was purified by column chromatography (stationary phase:silica gel; eluent: a 1:1 mixture of benzene and ethyl acetate) to obtain 0.50 g of diphenylmethyl 7β-[D(−)-α-(4-ethyl-2,3-dioxo-1-piperazinecarboxamido)-α-(2-thienyl)-acetamido]-7α-methoxy-3-[5-(1-methyl-1,2,3,4-tetrazolyl)thiomethyl]-Δ³-cephem-4-carboxylate, yield 60.2%.

IR (KBr) $cm^{-1}$: νC=O 1775, 1705, 1675. NMR (CDCl₃) δvalues: 1.09 (3H, t, —CH₃), 3.20–3.65 (6H, m, >CH₂×3), 3.46 (3H, s, —CH₃), 3.65–4.65 (2H, m, >CH₂), 3.75 (3H, s, —CH₃), 4.31 (2H, ABq >CH₂), 4.97 (1H, s≯CH), 5.88 (1H, d≯CH), 6.80–7.47 (14H, —C₆H₅×2,

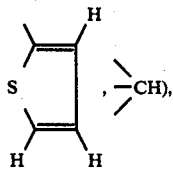

8.12 (1H, s, >NH), 9.72 (1H, d, >NH).

(2) In 2.0 ml of anisole was dissolved 0.3 g of diphenylmethyl 7β-[D(−)-α-(4-ethyl-2,3-dioxo-1-piperazinecarboxamido)-α-(2-thienyl)-acetamido)-7α-methoxy-3-[5-(1-methyl-1,2,3,4-tetrazolyl)thiomethyl]-Δ³-cephem-4-carboxylate. To the solution was added with ice-cooling 2.0 ml of trifluoroacetic acid and the mixture was stirred for 30 minutes at the same temperature. After completion of the reaction, the solvent was removed by distillation under reduced pressure. To the residue were added 5 ml of ethyl acetate and 5 ml of water and the pH of the solution was adjusted to 7.0 with an aqueous sodium hydrogen carbonate solution. The aqueous layer was separated and mixed with 10 ml of fresh methyl acetate, after which the pH thereof was adjusted to 2.0 with 2 N hydrochloric acid. The organic layer was separated, washed with water, dried over magnesium sulfate, and freed from the solvent by distillation under reduced pressure. The residue was washed with diethyl ether to obtain 0.20 g of white 7β-[D(−)-α-(4-ethyl-2,3-dioxo-1-piperazinecarboxamido)-α-(2-thienyl)-acetamido]-7α-methoxy-3-[5-(1-methyl-1,2,3,4-tetrazolyl)thiomethyl]-Δ³-cephem-4-carboxylic acid, yield 83.3%.

IR (KBr) cm⁻¹: νC=O 1770, 1705, 1695, 1675. NMR (DMSO-d₆) δvalues: 1.12 (3H, t, —CH₃), 3.20–3.70 (6H, m, >CH₂×3), 3.46 (3H, s, —CH₃), 3.70–4.35 (4H, m, >CH₂×2), 3.95 (3H, s, —CH₃), 5.03 (1H, s,>CH), 5.80 (1H, d,>CH), 6.95–7.30 (2H, m,

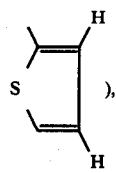

7.40–7.55 (1H, m,

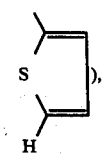

9.70–9.90 (2H, m, >NH×2).

In a similar manner, the following compounds were obtained:

7β-[D(−)-α-(4-ethyl-2,3-dioxo-1-piperazine-carboxamido)-α-(2-thienyl)-acetamido]-7α-methoxy-3-[5-(1-carboxymethyl-1,2,3,4-tetrazolyl)thiomethyl]-Δ³-cephem-4-carboxylic acid, m.p. 160° C. (decomp.).

IR (KBr) cm⁻¹: νC=O 1770, 1705, 1670. NMR (DMSO—d₆) δvalues: 1.09 (3H, t, —CH₃), 3.11—3.72 (6H, m, >CH₂×3), 3.41 (3H, s, —CH₃), 3.76–4.60 (4H, m, >CH₂×2), 5.04 (1H, s, CH), 5.26 (2H, s, >CH₂), 5.90 (1H, d, CH), 6.92–7.26 (2H, m,

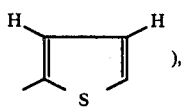

7.39–7.50 (1H, m,

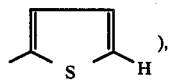

9.68–9.79 (2H, m, >NH×2)

7β-[D(−)-α-(4-ethyl-2,3-dioxo-1-piperazine-carboxamido)-α-(2-thienyl)-acetamido]-7α-methoxy-3-acetoxymethyl-Δ³-cephem-4-carboxylic acid, m.p. 150°–165° C. (decomp.).

IR (KBr) cm⁻¹: νC=O 1775, 1720, 1705, 1675. NMR (DMSO-d₆) δvalues: 1.07 (3H, t, —CH₃), 2.00 (3H, s, —CH₃), 3.19–3.72 (6H, m, >CH₂×3), 3.42 (3H, s, —CH₃), 3.74–4.12 (2H, m, >CH₂), 4.75 (2H, ABq, >CH₂), 5.10 (1H, s,>CH), 5.89 (1H, d,>CH), 6.89–7.22 (2H, m,

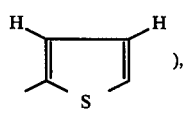

7.40–7.51 (1H, m,

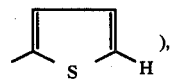

9.65 (1H, d, >NH), 9.81 (1H, s, >NH).

EXAMPLE 2

In 15 ml of water were suspended 1 g of the 7β-[D(−)-α-(4-ethyl-2,3-dioxo-1-piperazinecarboxamido)-α-(2-thienyl)-acetamido]-7α-methoxy-3-acetoxymethyl-Δ³-cephem-4-carboxylic acid obtained in Example 1 and 0.34 g of 5-mercapto-1-carbamoylmethyl-1,2,3,4-tetrazole. To the suspension was added 0.28 g of sodium hydrogen carbonate with stirring. The resulting solution was allowed to react at 55°–60° C. for 20 hours, while adjusting the pH of the reaction system to 6.0–6.3. After completion of the reaction, 20 ml of methyl acetate was added to the reaction mixture and the pH of the solution was adjusted to 2 by the dropwise addition of 2 N hydrochloric acid. The methyl acetate layer was separated and the aqueous layer was extracted three times with 15-ml portions of methyl acetate. The organic layers were combined, dried over anhydrous magnesium sulfate, and evaporated to dryness. The residue was dissolved in 20 ml of acetone. Diphenyldiazomethane was added dropwise with stirring to the resulting solution until the color had persisted. The solution was freed from the solvent by distillation under reduced pressure and the residue was purified by column chromatography (stationary phase:silica gel; eluent: 1:3 mixture of benzene and ethyl acetate) to obtain diphenylmethyl 7β-[D(−)-α-(4-ethyl-2,3-dioxo-1- piperazinecarboxamido)-α-(2-thienyl)-acetamide]-7α-methoxy-3-[5-(1-carbamoylmethyl-1,2,3,4-tetrazolyl)-thiomethyl]-Δ³-cephem-4-carboxylate in faintly yellow powder form. To this compound were added with ice-cooling 3 ml of anisole and 3 ml of trifluoroacetic acid. The mixture was allowed to react for 60 minutes with ice-cooling. After completion of the reaction, the reaction mixture was freed from the solvent by distillation under reduced pressure. To the residue was added 10 ml of ethyl acetate and the precipitated crystals were collected by filtration to obtain 0.32 g of 7β-[D(−)-α-(4-ethyl-2,3-dioxo-1-piperazinecarboxido)-α-(2-thienyl)-acetamido]-7α-methoxy-3-[5-(1-carbamoylmethyl-1,2,3,4-tetrazolyl)thiomethyl]-Δ³-cephem-4-carboxylic acid, m.p. 145°–150° C. (decomp.), yield 27.6%.

IR (KBr) cm⁻¹: νC=O 1775, 1670–1720. NMR (DMSO-d₆) δvalues: 1.10 (3H, t, —CH₃), 3.20–4.10 (8H, m, >CH₂×4), 3.44 (3H, s, CH₃O—), 4.34 (2H, ABq, >CH₂), 5.10 (2H, s, >CH₂), 5.19 (1H, s, ⇀CH), 5.95 (1H, d, ⇀CH), 6.91–7.88 (5H, m,

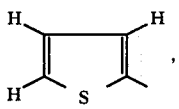

—CONH₂), 9.70 (1H, d, >NH), 9.85 (1H, d, >NH)

In a similar manner, the following compounds were obtained:

7β-[D(−)-α-(4-ethyl-2,3-dioxo-1-piperazine-carboxamido)-α-(2-thienyl)-acetamido]-7α-methoxy-3-{5-[1-(2-hydroxyethyl)-1,2,3,4-tetrazolyl]thiomethyl}-Δ³-cephem-4-carboxylic acid, m.p. 125°–130° C. (decomp.).

IR (KBr) cm⁻¹: νC=O 1770, 1720–1670. NMR (DMSO-d₆) δvalues: 1.12 (3H, t, —CH₃), 3.20–4.50 (14H, m, >CH₂×7), 3.40 (3H, s, CH₃O—), 5.00 (1H, s,⇀CH), 5.85 (1H, d,⇀CH), 6.85–7.60 (3H, m,

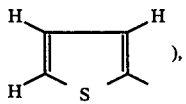

9.70 (1H, d, >NH), 9.85 (1H, s, >NH).

7β-[D(−)-α-(4-ethyl-2,3-dioxo-1-piperazinecarboxamido)-α-(2-thienyl)-acetamido]-7α-methoxy-3-[3-(6-hydroxypyridazinyl)-Δ³-cephem-4-carboxylic acid, m.p. 155°–160° C. (decomp.).

IR (KBr) cm⁻¹: νC=O 1765, 1700, 1665. NMR (DMSO-d₆) δvalues: 1.10 (3H, t, —CH₃), 3.20–4.30 (10H, m, >CH₂×5), 3.41 (3H, s, CH₃O—), 5.02 (1H, s,⇀CH), 5.85 (1H, d,⇀CH), 6.70–7.50 (5H, m,

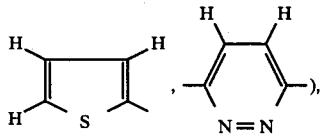

9.70 (1H, d, >NH), 9.85 (1H, s, >NH)

7β-[D(−)-α-(4-ethyl-2,3-dioxo-1-piperazinecarboxamido)-α-(2-thienyl)-acetamido]-7α-methoxy-3-[5-(2-methyl-1,2,3,4-tetrazolyl)thiomethyl]-Δ³-cephem-4-carboxylic acid, m.p. 165°–174° C. (decomp.)

IR (KBr) cm⁻¹: νC=O 1770, 1710, 1670. NMR (DMSO-d₆) δvalues: 1.07 (3H, t, —CH₃), 3.20–3.76 (6H, m, >CH₂×3), 3.41 (3H, s, CH₃O—), 3.76–4.20 (4H, m, >CH₂×2), 4.39 (3H, s, >N—CH₃), 5.04 (1H, s,⇀CH), 5.90 (1H, d,⇀CH), 6.89–7.25 (2H, m,

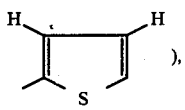

7.35–7.48 (1H, m,

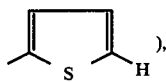

9.60–9.77 (2H, m, >NH×2)

7β-[D(−)-α-(4-ethyl-2,3-dioxo-1-piperazinecarboxamido)-α-(2-thienyl)-acetamido]-7α-methoxy-3-[5-(1,3,4-thiadiazolyl)thiomethyl]-Δ³-cephem-4-carboxylic acid, m.p. 160°–175° C. (decomp.)

IR (KBr) cm⁻¹: νC=O 1780, 1710, 1675. NMR (DMSO-d₆) δvalues: 1.09 (3H, t, —CH₃), 3.21–3.75 (6H, m, >CH₂×3), 3.43 (3H, s, CH₃O—), 3.75–4.10 (2H, m, >CH₂), 4.40 (2H, ABq, >CH₂), 5.14 (1H, s,⇀CH), 5.94 (1H, d,⇀CH), 6.91–7.39 (2H, m,

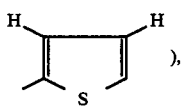

7.40–7.53 (1H, m,

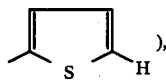

9.53

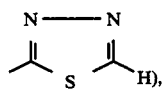

9.65–9.84 (2H, m, >NH×2)

7β-[D(−)-α-(4-ethyl-2,3-dioxo-1-piperazinecarboxamido)-α-(2-thienyl)-acetamido]-7α-methoxy-3-[5-(1-vinyl-1,2,3,4-tetrazolyl)thiomethyl]-Δ³-cephem-4-carboxylic acid, m.p. 150°–153° C. (decomp.)

IR (KBr) cm⁻¹: νC=O 1770, 1710, 1700, 1665. NMR (DMSO-d₆) δvalues: 1.10 (3H, t, —CH₃), 3.20–3.70 (6H, m, >CH₂×3), 3.43 (3H, s, —CH₃), 3.80–4.55 (4H, m, >CH₂×2), 5.10 (1H, s,⇀CH), 5.46 (1H, d, =CH—), 5.83 (1H, d, =CH—), 5.94 (1H, d,⇀CH), 6.90–7.52 (4H, m,

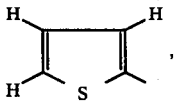

=CH—), 9.70 (1H, d, >NH), 9.86 (1H, s, >NH).

7β-[D(−)-α-(4-ethyl-2,3-dioxo-1-piperazinecarboxamido)-α-(2-thienyl)-acetamido]-7α-methoxy-3-{5-[1-(2-hydroxyiminopropyl)-1,2,3,4-tetrazolyl]thiomethyl}-

Δ³-cephem-4-carboxylic acid, m.p. 165°–172° C. (decomp.)

IR (KBr) cm⁻¹: νC═O 1775, 1705, 1675. NMR (DMSO-d₆) δvalues: 1.09 (3H, t, —CH₃), 1.58 (1.7H, s, —CH₃), 1.76 (1.3H, s, —CH₃), 3.18–3.69 (6H, m, >CH₂×3), 3.49 (3H, s, —CH₃), 3.77–4.20 (4H, m, >CH₂×2), 5.05 (3H, m, CH, >CH₂), 8.57 (1H, d, CH), 6.85–7.25 (2H, m,

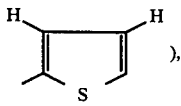

), 7.40–7.44 (1H, m,

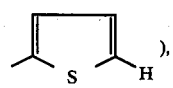

), 9.60 (1H, d, >NH), 9.65 (1H, s, >NH)

7β-[D(—)-α-(4-ethyl-2,3-dioxo-1-piperazinecarboxamido)-α-(2-thienyl)-acetamido]-7α-methoxy-3-[5-(1-acetylmethyl-1,2,3,4-tetrazolyl)thiomethyl]-Δ³-cephem-4-carboxylic acid, m.p. 164°–175° C. (decomp.)

IR (KBr) cm⁻¹: νC═O 1775, 1720, 1705, 1675. NMR (DMSO-d₆) δvalues: 1.10 (3H, t, —CH₃), 2.27 (3H, s, —CH₃), 3.10–3.70 (6H, m, >CH₂×3), 3.43 (3H, s, —CH₃), 3.75–4.20 (4H, m, >CH₂×2), 4.40 (2H, s, >CH₂), 5.00 (1H, s, CH), 5.45 (1H, d, CH), 6.95–7.32 (2H, m,

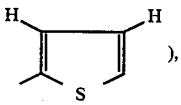

), 7.40–7.47 (1H, m,

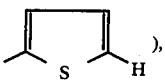

), 9.45–9.67 (2H, m, >NH×2)

7β-[D(—)-α-(4-ethyl-2,3-dioxo-1-piperazinecarboxamido)-α-(2-thienyl)-acetamido]-7α-methoxy-3-{5-[1-(hydroxyaminocarbonylmethyl)-1,2,3,4-tetrazolyl]thiomethyl}-Δ³-cephem-4-carboxylic acid, m.p. 160°–170° C. (decomp.)

IR (KBr) cm⁻¹: νC═O 1770, 1710, 1700, 1665. NMR (DMSO-d₆) δvalues: 1.11 (3H, t, —CH₃), 3.20–3.70 (6H, m, >CH₂×3), 3.40 (3H, s, —CH₃), 3.80–4.65 (4H, m, >CH₂×2), 5.07 (1H, s, CH), 5.28 (2H, s, >CH₂), 5.90 (1H, d, CH), 6.90–7.50 (3H, m,

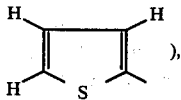

), 9.67 (1H, d, >NH), 9.81 (1H, s, >NH).

EXAMPLE 3

In 10 ml of aqueous solution containing 0.27 g of sodium hydrogen carbonate were dissolved 1 g of 7β-[D(—)-α-(4-ethyl-2,3-dioxo-1-piperazinecarboxamido)-α-(2-thienyl)-acetamido]-7α-methoxy-3-acetoxymethyl-Δ³-cephem-4-carboxylic acid and 0.17 g of 5-mercapto-1,2,3,4-tetrazole. After the pH of the solution had been adjusted to 6.4, the solution was allowed to react at 60° C. for 20 hours. To the reaction mixture were added 10 ml of methyl acetate and 5 ml of ethyl acetate. After the pH thereof was adjusted to 2.2 with 2 N hydrochloric acid, the organic layer was washed twice with 10-ml portions of water, dried over magnesium sulfate and freed from the solvent by distillation under reduced pressure. The residue was purified by column chromatography (stationary phase: silica gel; eluent: a 1:2 mixture of benzene and ethyl acetate) to obtain 0.39 g of 7β-[D(—)-α-(4-ethyl-2,3-dioxo-1-piperazinecarboxamido)-α-(2-thienyl)-acetamido]-7α-methoxy-3-[5-(1,2,3,4-tetrazolyl)thiomethyl]-Δ³-cephem-4-carboxylic acid, m.p. 178°–183° C. (decomp.), yield 36.48%.

IR (KBr) cm⁻¹: νC═O 1770, 1690, 1670. NMR (DMSO-d₆) δvalues: 1.08 (3H, t, —CH₃), 3.18–3.70 (6H, m, >CH₂×3), 3.40 (3H, s, CH₃O—), 3.70–4.10 (4H, m, >CH₂×2), 5.07 (1H, s,→CH), 5.89 (1H, d,→CH), 6.87–7.20 (2H, m,

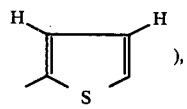

), 7.39–7.50 (1H, m,

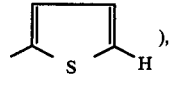

), 9.65 (1H, d, >NH), 9.81 (1H, s, >NH)

In a similar manner, the following compound was obtained:

7β-[D(—)-α-(4-ethyl-2,3-dioxo-1-piperazinecarboxamido)-α-(2-thienyl)-acetamido]-7α-methoxy-3-[5-(1,2,3-triazolyl)thiomethyl]-Δ³-cephem-4-carboxylic acid, m.p. 178°–190° C. (decomp.)

IR (KBr) cm⁻¹: νC═O 1770, 1695, 1680. NMR (DMSO-d₆) δvalues: 1.10 (3H, t, —CH₃), 3.20–3.70 (6H, m, >CH₂×3), 3.40 (3H, s, CH₃O—), 3.80–4.20 (4H, m, >CH₂×2), 5.10 (1H, s,→CH), 5.91 (1H, d,→CH), 6.88–7.20 (2H, m,

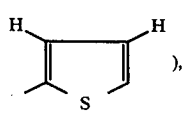

), 7.37–7.50 (1H, m,

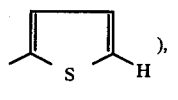

), 7.90 (1H, s,

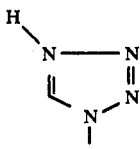

9.58–9.74 (2H, m, >NH×2)

EXAMPLE 4

In 10 ml of an aqueous solution containing 0.27 g of sodium hydrogen carbonate were dissolved 1 g of 7β-[D(−)-α-(4-ethyl-2,3-dioxo-1-piperazinecarboxamido)-α-(2-thienyl)-acetamido]-7α-methoxy-3-acetoxymethyl-Δ³-cephem-4-carboxylic acid and 0.32 g of the sodium salt of 1-(2-dimethylaminoethyl)-5-mercapto-1,2,3,4-tetrazole. While maintaining the pH at 6.2–6.5, the solution was allowed to react at 60° C. for 16 hours. The reaction mixture was purified by column chromatography (stationary phase: 20 g of Amberite XAD-2; eluted with 100 ml of water and then with 100 ml of 50% aqueous solution of methanol). The eluate was evaporated to dryness, to obtain 0.32 g of sodium 7β-[D(−)-α-(4-ethyl-2,3-dioxo-1-piperazinecarboxamido)-α-(2-thienyl)-acetamido]-7α-methoxy-3-{5-[1-(2-dimethylaminoethyl)-1,2,3,4-tetrazolyl]thiomethyl}-Δ³-cephem-4-carboxylate in white powder form, m.p. 166°–175° C. (decomp.), yield 26.17%.

IR (KBr) cm$^{-1}$: νC≡O 1760, 1705, 1670, 1610. NMR (DMSO-d$_6$) δvalues: 1.10 (3H, t, —CH$_3$), 2.20 (6H, m, —CH$_3$×2), 2.68 (2H, t, >CH$_2$), 3.20–3.70 (6H, m, >CH$_2$×3), 3.40 (3H, s, CH$_3$O—), 3.72–4.30 (6H, m, >CH$_2$×3), 5.05 (1H, s,→CH), 5.91 (1H, d,→CH), 6.90–7.30 (2H, m,

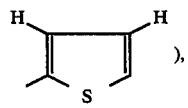

7.40–7.51 (1H, m,

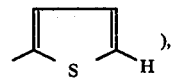

9.6–9.75 (2H, m, >NH×2)

In a similar manner, the following compounds were obtained:

Sodium 7β-[D(−)-α-(4-ethyl-2,3-dioxo-1-piperazinecarboxamido)-α-(2-thienyl)-acetamido]-7α-methoxy-3-{5-[2-(2-dimethylaminoethyl)-1,2,3,4-tetrazolyl]thiomethyl}-Δ³-cephem-4-carboxylate, m.p. 175°–183° C. (decomp.).

IR (KBr) cm$^{-1}$: νC≡O 1760, 1705, 1670, 1615. NMR (DMSO-d$_6$) δvalues: 1.11 (3H, t, —CH$_3$), 2.24 (6H, m, —CH$_3$×2), 2.83 (2H, t, >CH$_2$), 3.20–3.70 (6H, m, >CH$_2$×3), 3.42 (3H, s, CH$_3$O—), 3.70–4.20 (4H, m, >CH$_2$×2), 4.60 (2H, t, >CH$_2$), 5.0 (1H, s,→CH), 5.92 (1H, d,→CH), 6.90–7.30 (2H, m,

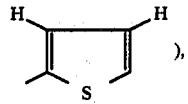

7.37–7.48 (1H, m,

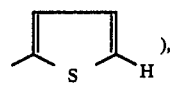

9.6–9.75 (2H, m, >NH×2)

Sodium 7β-[D(−)-α-(4-ethyl-2,3-dioxo-1-piperazinecarboxyamido)-α-(2-thienyl)-acetamido]-7α-methoxy-3-{5-[1-(2-aminoethyl)-1,2,3,4-tetrazolyl]thiomethyl}-Δ³-cephem-4-carboxylate, m.p. 180°–187° C. (decomp.)

IR (KBr) cm$^{-1}$: νC≡O 1765, 1705, 1670, 1600. NMR (DMSO-d$_6$) δvalues: 1.10 (3H, t, —CH$_3$), 3.23–3.74 (6H, m, >CH$_2$×3), 3.45 (3H, s, —CH$_3$), 3.77–4.87 (6H, m, >CH$_2$×3), 4.81 (2H, t, >CH$_2$), 5.07 (1H, s,→CH), 5.45 (1H, d,→CH), 6.95–7.25 (2H, m,

7.40–7.52 (1H, m,

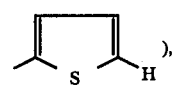

9.61–9.80 (2H, m, >NH×2).

EXAMPLE 5

(1) To an ice-cooled suspension of 2.55 g of DL-α-amino-2-furylacetic acid in 35 ml of methylene chloride was added 4.81 ml of trimethylchlorosilane. To the resulting mixture was added dropwise 5.04 ml of triethylamine over a period of 10 minutes at 5° to 10° C. The reaction was allowed to proceed at 15° to 20° C. for one hour. To the reaction mixture was added over a period of 15 minutes at 5° to 10° C. 7.01 g of a mixture of 4-ethyl-2,3-dioxo-1-piperazinecarbonyl chloride and triethylamine hydrochloride, said mixture containing 58.02% of the former. The reaction was allowed to proceed at 10° to 15° C. for one hour. After addition of 20 ml of water, the reaction mixture was stirred at room temperature for one hour, then at 5° to 7° C. for 30 minutes. The precipitated crystals were collected by filtration, washed with 5 ml of methylene chloride and 5 ml of water in this order, and then dried to obtain 4.75 g of DL-α-(4-ethyl-2,3-dioxo-1-piperazinecarboxamido)-2-furylacetic acid, m.p. 179°–181° C. (decomp.), yield 85.6%.

IR (KBr) cm$^{-1}$: νC≡O 1735, 1709, 1650.

NMR DMSO-d$_6$) δvalues: 1.09 (3H, t, —CH$_3$), 3.18–3.71 (4H, m, >CH$_2$×2), 3.78–4.09 (2H, m, >CH$_2$), 5.53 (1H, d,→CH), 6.44 (2H, m,

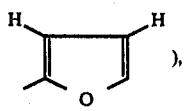

7.61 (1H, s,

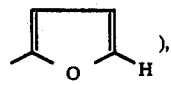

9.69 (1H, d, >NH).

(2) In 15 ml of anhydrous methylene chloride was suspended 0.94 g of DL-α-(4-ethyl-2,3-dioxo-1-piperazinecarboxamido)-2-furylacetic acid. To the suspension was added 0.35 ml of N-methylmorpholine with ice-cooling to form a homogeneous solution. To the solution cooled to −20° C. was added dropwise over a period of 5 minutes a solution of 0.32 ml of ethyl chlorocarbonate in 2 ml of anhydrous methylene chloride. The mixture was stirred at −15° C. for 60 minutes. To the mixture again cooled to −20° C. was added dropwise over a period of 10 minutes a solution of 1.50 g of diphenylmethyl 7-amino-3-[5-(1-methyl-1,2,3,4-tetrazolyl)thiomethyl]-$\Delta^3$-cephem-4-carboxylate in 15 ml of anhydrous methylene chloride. The mixture was further stirred at −10° C. for 90 minutes. After the temperature of the reaction mixture had been elevated to room temperature, the reaction mixture was poured into 10 ml of water and the organic layer was separated, and 10 ml of fresh water was added thereto, after which the pH thereof was adjusted to 6.5 with aqueous solution of sodium hydrogen carbonate. The organic layer was separated, washed with 10 ml of water and 10 ml of saturated sodium chloride solution in this order and dried over magnesium sulfate. After removing the solvent by distillation under reduced pressure, the residue was treated with diethyl ether to obtain 2.0 g of a white powder. By a thin layer chromatography [developer: a benzene-ethyl acetate mixture (1:3)], it was found that this comprised two components (Rf: 0.28 and 0.24). The white powder was subjected to elution by a column chromatography [stationary phase: silica gel; eluent: a benzene-ethyl acetate mixture (2:1)] to isolate the component corresponding to the upper zone component in the thin layer chromatography and the component corresponding to the lower zone component in the thin layer chromatography, the amount of the two components isolated having been 1.1 g in total.

The upper zone component (presumably, diphenylmethyl 7-[D-α-(4-ethyl-2,3-dioxo-1-piperazinecarboxamido)-α-(2-furyl)-acetamido]-3-[5-(1-methyl-1,2,3,4-tetrazolyl)thiomethyl]-$\Delta^3$-cephem-4-carboxylate), m.p. 128°–138° C. (decomp.)

IR (KBr) cm$^{-1}$: $\nu$C═O 1800, 1705, 1680. NMR (CDCl$_3$) δvalues: 1.11 (3H, t, —CH$_3$), 3.30–4.30 (10H, m, >CH$_2$×5), 3.76 (3H, s, —CH$_3$), 4.91 (1H, d,→CH), 5.72–5.93 (2H, m,→CH×2), 6.25 (2H, m,

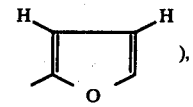

6.82 (1H, s, CH), 7.20–7.53 (12H, m, —C$_6$H$_5$×2,

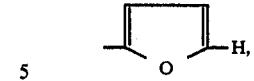

>NH), 9.80 (1H, d, >NH).

The lower zone component (presumably, diphenylmethyl 7-[L-α-(4-ethyl-2,3-dioxo-1-piperazinecarboxamido)-α-(2-furyl)-acetamido]-3-[5-(1-methyl-1,2,3,4-tetrazolyl)thiomethyl]-$\Delta^3$-cephem-4-carboxylate), m.p. 128°–136° C. (decomp.)

IR (KBr) cm$^{-1}$: $\nu$C═O 1800, 1705, 1680. NMR (CDCl$_3$) δvalues: 1.08 (3H, t, —CH$_3$), 3.20–4.30 (10H, m, >CH$_2$×5), 3.86 (3H, s, —CH$_3$), 5.00 (1H, d,→CH), 5.61 –5.98 (2H, m,→CH×2), 6.31 (2H, m,

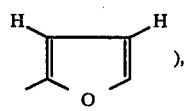

6.83 (1H, s,→CH), 7.29 (11H, m, —C$_6$H$_5$×2,

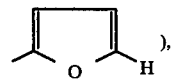

7.94 (1H, d, >NH), 9.88 (1H, d, >NH)

(3) In a mixture of 14 ml of anhydrous chloroform and 3.5 ml of anhydrous tetrahydrofuran was dissolved 0.86 g of the upper zone component obtained in (2). To the solution cooled to −75° C. was added 1.97 ml of a solution of lithium methoxide (1.948 mmoles/ml) in methanol and the resulting mixture was stirred for 3 minutes at −75° C. After addition of 0.20 ml of tert.-butyl hypochlorite, the mixture was stirred at −70° to −65° C. for 15 minutes. After addition of 0.20 ml of acetic acid, the temperature of the reaction system was elevated to room temperature. The reaction mixture was freed from the solvent by distillation under reduced pressure and the residue was dissolved in a mixture of 10 ml of ethyl acetate and 10 ml of water. The organic layer was separated, and 10 ml of water, was added thereto, after which the pH thereof was adjusted to 2.5 with 2 N hydrochloric acid. The organic layer was separated, washed twice with 10-ml portions of saturated sodium chloride solution, dried over magnesium sulfate, and freed from the solvent by distillation under reduced pressure. The residue was purified by column chromatography [stationary phase: 15 g of silica gel; eluent: a benzene-ethyl acetate mixture (2:1)] to obtain 0.30 g of a white powder.

The white powder thus obtained was dissolved in 3.0 ml of anisole, and 3.0 g of trifluoroacetic acid was added to the solution with ice-cooling. The resulting mixture was stirred for 30 minutes at the same temperature. After removal of the solvent by distillation under reduced pressure, 5 ml of ethyl acetate and 5 ml of water were added to the residue, and a saturated sodium hydrogen carbonate was then added thereto with stirring to adjust the pH thereof to 6.5, upon which the residue was dissolved. The aqueous layer was separated, and 10 ml of methyl acetate was added thereto, after which the pH thereof was adjusted to 2.0 with 2 N hydrochloric acid, and the organic layer was separated. The aqueous layer was further extracted with 10 ml of methyl acetate and the extract was combined with the organic layer obtained above. The combined organic layer was washed twice with 10-ml portions of saturated sodium chloride solution, dried over magnesium sulfate, and freed from the solvent by distillation under reduced pressure. The residue was treated with diethyl ether to obtain 0.17 g of 7β-[D-α-(4-ethyl-2,3-dioxo-1-piperazinecarboxamido)-α-(2-furyl)-acetamido]-7α-methoxy-3-[5-(1-methyl-1,2,3,4-tetrazolyl)thiomethyl]-Δ³-cephem-4-carboxylic acid in white powder form, m.p. 130°–138° C. (decomp.), yield 70.8%.

IR (KBr) cm⁻¹: νC=O 1770, 1700, 1670. NMR (DMSO-d₆) δvalues: 1.07 (3H, t, —CH₃), 3.28-4.01 (8H, m, >CH₂×4), 3.38 (3H, s, —CH₃), 3.88 (3H, s, —CH₃), 4.10-4.45 (2H, m, >CH₂), 5.03 (1H, s,→CH), 5.73 (1H, d,→CH), 6.39 (2H, m,

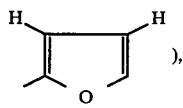

), 7.54 (1H, bs,

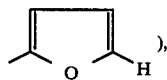

), 9.51-9.70 (2H, m, >NH×2)

In a similar manner, the following compounds were obtained:

7β-[D-α-(4-ethyl-2,3-dioxo-1-piperazinecarboxamido)-α-(2-furyl)-acetamido]-7α-methoxy-3-[5-(1-carbamoylmethyl-1,2,3,4-tetrazolyl)thiomethyl]-Δ³-cephem-4-carboxylic acid.

7β-[D-α-(4-ethyl-2,3-dioxo-1-piperazinecarboxamido)-α-(2-furyl)-acetamido]-7α-methoxy-3-{5-[1-(2-hydroxyethyl)-1,2,3,4-tetrazolyl]thiomethyl}-Δ³-cephem-4-carboxylic acid.

7β-[D-α-(4-ethyl-2,3-dioxo-1-piperazinecarboxamido)-α-(2-furyl)-acetamido]-7α-methoxy-3-[5-(1-vinyl-1,2,3,4-tetrazolyl)thiomethyl]-Δ³-cephem-4-carboxylic acid.

EXAMPLE 6

(1) To a suspension of 2.5 g of D(—)-α-amino-1,4-cyclohexadienylacetic acid in 20 ml of water was added dropwise with ice-cooling 2.3 ml of triethylamine to form a solution. To the solution at 5° to 10° C. was added dropwise 6.3 g of 4-ethyl-2,3-dioxo-1-piperazinecarbonyl chloride (58.02% in purity) over a period of 30 minutes, while adjusting the pH to 6.5-8.0 with 2.5 ml of triethylamine. The mixture was stirred at 10° to 15° C. for a further 30 minutes. The reaction mixture was washed with 20 ml of ethyl acetate, and 30 ml of fresh ethyl acetate was added thereto, after which the pH thereof was adjusted to 2.2 with 6 N hydrochloric acid. The organic layer was separated and the aqueous layer was further extracted with 15 ml of ethyl acetate. The extract was combined with the above organic layer, washed twice with 20-ml portions of water, then with 20 ml of saturated aqueous sodium chloride solution. The washed organic layer was dried over magnesium sulfate, and freed from the solvent by distillation under reduced pressure to obtain 4.2 g of D(—)-α-(4-ethyl-2,3-dioxo-1-piperazinecarboxamido)-1,4-cyclohexadienylacetic acid in white powder form, m.p. 104°–108° C., yield 80.0%

IR (KBr) cm⁻¹: νC=O 1705, 1670. NMR (DMSO-d₆) δvalues: 1.10 (3H, t, —CH₃), 2.61 (4H, m, >CH₂×2), 3.18-3.69 (4H, m, >CH₂×2), 3.70-4.13 (3H, m, >CH₂,→CH), 4.56 (1H, d,→CH), 5.60 (2H, m, CH×2), 5.70 (1H, s, CH), 9.49 (1H, d, >NH)

(2) To a solution of 2.3 g of D(—)-α-(4-ethyl-2,3-dioxo-1-piperazinecarboxamido)-1,4-cyclohexadienylacetic acid in 20 ml of anhydrous methylene chloride was added at −20° C. 0.79 ml of N-methylmorpholine. To the mixture was added dropwise 0.75 ml of ethyl chlorocarbonate over a period of 5 minutes at −20° to −15° C. To the mixture which had been stirred for a further 60 minutes at −20° to −15° C. was added dropwise over a period of 15 minutes at −20° C. a solution of 3.0 g of diphenylmethyl 7-amino-3-[5-(1-methyl-1,2,3,4-tetrazolyl)thiomethyl]-Δ³-cephem-4-carboxylate in 30 ml of anhydrous methylene chloride. The mixture was stirred for a further 120 minutes at −10° C. The reaction mixture was poured into 50 ml of water and the organic layer was separated. To the organic layer was added 30 ml of water and the pH thereof was adjusted to 7.0 with saturated aqueous sodium hydrogen carbonate solution. Thereafter, the organic layer was separated, washed with 30 ml of water and 30 ml of saturated aqueous sodium chloride solution in this order, dried over magnesium sulfate, and freed from the solvent by distillation under reduced pressure. To the residue was added 30 ml of benzene, and the precipitated crystals were collected by filtration to obtain 3.9 g of diphenylmethyl 7β-[D(—)-α-(4-ethyl-2,3-dioxo-1-piperazinecarboxamido)-α-(1,4-cyclohexadienyl)-acetamido]-3-[5-(1-methyl-1,2,3,4-tetrazolyl)thiomethyl]-Δ³-cephem-4-carboxylate, m.p. 151°–155° C.; yield 80.7%.

IR (KBr) cm⁻¹: νC=O 1770, 1700, 1665. NMR (CDCl₃) δvalues: 1.15 (3H, t, —CH₃), 2.62 (4H, m, >CH₂×2), 3.23-3.70 (6H, m, >CH₂×3), 3.71 (3H, s, —CH₃), 3.70-4.35 (4H, m, >CH₂×2), 4.92-5.28 (2H, m,→CH×2), 5.57 (2H, m,→CH×2), 5.75-5.97 (2H, m, →CH×2), 6.78 (1H, s,→CH), 7.75 (11H, m, —C₆H₅×2, >NH), 9.57 (1H, d, >NH).

(3) In a mixture of 15 ml of anhydrous chloroform and 4 ml of anhydrous tetrahydrofuran was dissolved 0.80 g of diphenylmethyl 7β-[D(—)-α-(4-ethyl-2,3-dioxo-1-piperazinecarboxamido)-α-(1,4-cyclohexadienyl)-acetamido]-3-[5-(1-methyl-1,2,3,4-tetrazolyl)thiomethyl)-Δ³-cephem-4-carboxylate. After addition of 1.0 g of "molecular sieve 3A", the solution was cooled to −70° C. To the solution was added 1.8 ml of a solution of lithium methoxide (1.948 mmoles/ml) in methanol and the mixture was stirred for 3 minutes at −70° C. Thereafter, 0.18 ml of tert.-butyl hypochlorite was added at one time and the mixture was stirred for 15 minutes at −70° to −65° C., and 0.2 ml of acetic acid was added thereto, after which the temperature of the mixture was elevated to room temperature. After removal of the molecular sieve by filtration, the reaction mixture was freed from the solvent by distillation under reduced pressure. The residue was dissolved by adding 20 ml of ethyl acetate and 10 ml of water, and the pH of the solution was adjusted to 6.5 with saturated aqueous sodium hydrogen carbonate solution. The organic layer was separated, and 10 ml of water was added thereto, after which the pH thereof was adjusted to 2.5 with 6 N hydrochloric acid. The organic layer was again separated, washed with 10 ml of water and 10 ml of saturated aqueous sodium chloride solution in this order, and freed from the solvent by distillation under reduced pressure. The residue was purified by column chromatography [stationary phase: silica gel; eluent: benzene-ethyl acetate mixture (2:1)]. After removal of the solvent from the eluate by distillation under reduced pressure, the residue was treated with diethyl ether to obtain 0.5 g of diphenylmethyl 7β-[D(−)-α-(4-ethyl-2,3-dioxo-1-piperazinecarboxamido)-α-(1,4-cyclohexadienyl)-acetamido]-7α-methoxy-3-[5-(1-methyl-1,2,3,4-tetrazolyl)-thiomethyl]-Δ³-cephem-4-carboxylate in white powder form, yield 60.3%.

IR (KBr) cm⁻¹: νC=O 1775, 1710, 1675. NMR (CDCl₃) δvalues: 1.17 (3H, t, —CH₃), 2.75 (4H, m, >CH₂×2), 3.29–3.68 (6H, m, >CH₂×3), 3.47 (3H, s, —CH₃), 3.77 (3H, s, —CH₃), 3.80–4.89 (4H, m, >CH₂×2), 4.99 (1H, s,>CH), 5.61 (2H, m>CH×2), 5.95 (1H, s,>CH), 6.87 (1H, s,>CH), 7.28–7.45 (11H, m, —C₆H₅×2, >NH), 9.55 (1H, d, >NH).

(4) In 5 ml of anisole was dissolved 0.4 g of diphenylmethyl 7β-[D(−)-α-(4-ethyl-2,3-dioxo-1-piperazinecarboxamido)-α-(1,4-cyclohexadienyl)-acetamido]-7α-methoxy-3-[5-(1-methyl-1,2,3,4-tetrazolyl)thiomethyl]-Δ³-cephem-4-carboxylate. To the solution was added 5 ml of trifluoroacetic acid with ice-cooling and the mixture was stirred for 30 minutes at the same temperature. After removal of the solvent from the reaction mixture, 10 ml of methyl acetate and 10 ml of water were added to the residue and the pH thereof was adjusted to 6.5 by adding with stirring saturated aqueous sodium hydrogen carbonate solution. The aqueous layer was separated, and 5 ml of methyl acetate was added thereto, after which the pH thereof was adjusted to 2.2 with 6 N hydrochloric acid, and the mixture was allowed to stand overnight in a refrigerator. The precipitated crystals were collected by filtration, washed twice with 5-ml portions of water, then with 3 ml of methyl acetate, and dried to obtain 0.2 g of 7β-[D(−)-α-(4-ethyl-2,3-dioxo-1-piperazinecarboxamido)-α-(1,4-cyclohexadienyl)-acetamido]-7α-methoxy-3-[5-(1-methyl-1,2,3,4-tetrazolyl)]-Δ³-cephem-4-carboxylic acid, m.p. 177°–178° C. (decomp.), yield 62.7%.

IR (KBr) cm⁻¹: νC=O 1770, 1710, 1685. NMR (DMSO-d₆) δvalues: 1.10 (3H, t, —CH₃), 2.18 (4H, m, >CH₂×2), 3.34–3.73 (6H, m, >CH₂×3), 3.41 (3H, s, —CH₃), 3.79–4.37 (4H, m, >CH₂×2), 3.93 (3H, s, —CH₃), 4.97 (1H, d,>CH), 5.06 (1H, s,>CH), 5.61 (2H, m,>CH×2), 5.87 (1H, s,>CH), 9.38 (1H, d, >NH), 9.53 (1H, s, >NH).

In a similar manner, the following compounds were obtained:

7β-[D(−)-α-(4-ethyl-2,3-dioxo-1-piperazinecarboxamido)-α-(1,4-cyclohexadienyl)-acetamido]-7α-methoxy-3-acetoxymethyl-Δ³-cephem-4-carboxylic acid.

7β-[D(−)-α-(4-ethyl-2,3-dioxo-1-piperazinecarboxamido)-α-(1,4-cyclohexadienyl)-acetamido]-7α-methoxy-3-[2-(5-methyl-1,3,4-thiadiazolyl)thiomethyl]-Δ³-cephem-4-carboxylic acid.

EXAMPLE 7

(1) In 15 ml of anhydrous methylene chloride was dissolved 2.0 g of α-(4-ethyl-2,3-dioxo-1-piperazinecarboxamido)-α-(2-trichloroethoxycarbonylamino-4-thiazolyl)-acetic acid. To the solution was added at −20° C. 0.43 ml of N-methylmorpholine. To the resulting mixture was added dropwise over a period of 5 minutes a solution of 0.41 ml of ethyl chlorocarbonate in 2 ml of methylene chloride, while maintaining the temperature at −20° to −25° C. The reaction was allowed to proceed for 1.5 hours at the same temperature. To the reaction mixture was added dropwise at −15° to −20° C. over a period of 15 minutes a solution of 2.0 g of diphenylmethyl 7-amino-3-[5-(1-methyl-1,2,3,4-tetrazolyl)thiomethyl)-Δ³-cephem-4-carboxylate in 30 ml of anhydrous methylene chloride. The reaction was effected for 2 hours at −10° to −15° C. After the temperature of the reaction mixture was elevated to room temperature, the reaction mixture was poured into 30 ml of water, and the pH thereof was adjusted to 6.5 with saturated aqueous solution of sodium hydrogen carbonate. The organic layer was separated, and 30 ml of water was freshly added thereto, after which the pH thereof was adjusted to 2.0 with 6 N hydrochloric acid. The organic layer was separated, washed with 30 ml of water and 30 ml of saturated aqueous sodium chloride solution in this order, dried over magnesium sulfate, and freed from the solvent by distillation under reduced pressure to obtain 3.3 g of white foamy residue. By a thin layer chromatography (developer: a 1:3 mixture of benzene and ethyl acetate), it was found that this comprised two components. The white foamy residue was subjected to elution by a column chromatography (stationary phase: silica gel; eluent: a 3:2 mixture of benzene and ethyl acetate) to obtain 1.3 g of a white powder melting at 166°–179° C. (decomp.), which corresponded to the upper zone component in the thin layer chromatography, and 1.4 g of a white powder melting at 180°–190° C. (decomp.), which corresponded to the lower zone component in the thin layer chromatography.

The upper zone compound: Presumably, diphenylmethyl 7-[D-α-(2-trichloroethoxycarbonylamino-4-thiazolyl)-α-(4-ethyl-2,3-dioxo-1-piperazinecarboxamido)-acetamido]-3-(5-(1-methyl-1,2,3,4-tetrazolyl)thiomethyl]-Δ³-cephem-4-carboxylate.

IR (KBr) cm⁻¹: νC=O 1780, 1710, 1685. NMR (CDCl₃) δvalues: 1.12 (3H, t, —CH₃), 2.90–3.87 (8H, m, >CH₂×4), 3.47 (3H, s, >N—CH₃), 4.12, 4.20 (2H, ABq, >CH₂), 4.24, 4.90 (2H, ABq, >CH₂), 5.04 (1H, d,>CH), 5.56 (1H, d,>CH), 5.98 (1H, d, d,>CH), 6.76 (1H, s,>CH), 6.89 (1H, s,>CH), 7.26 (11H, m, —C₆H₅×2, >NH), 8.62 (1H, bs, >NH), 9.70 (1H, d, >NH).

The lower zone component: Presumably, diphenylmethyl 7-[L-α-(2-trichloroethoxycarbonylamino-4-thiazolyl)-α-(4-ethyl-2,3-dioxo-1-piperazinecarboxamido)-acetamido]-3-[5-(1-methyl-1,2,3,4-tetrazolyl)thiomethyl]-Δ³-cephem-4-carboxylate.

IR (KBr) cm⁻¹: νC=O 1780, 1710, 1685. NMR (CDCl₃) δvalues: 1.05 (3H, t, —CH₃), 3.12–4.10 (8H, m, >CH₂×4), 3.81 (3H, s, —CH₃), 4.16, 4.23 (2H, ABq, >CH₂), 4.84 (2H, bs, >CH₂), 4.97 (1H, d,>CH), 5.67 (1H, d, d,>CH), 6.12 (1H, d,>CH), 6.75 (1H, s,>CH), 6.84 (1H, s,>CH), 7.23 (10H, s, —C₆H₅×2), 7.90–8.30 (2H, m, >NH×2), 9.79 (1H, d, >NH).

(2) In a mixture of 15 ml of anhydrous chloroform and 5 ml of anhydrous tetrahydrofuran was dissolved 1.2 g of the upper zone component obtained in (1). To the solution was added at −75° C. 2.17 ml of a solution of lithium methoxide (1.948 mmoles/ml) in methanol and the resulting mixture was stirred at −75° C. for 3 minutes. To the mixture was added at −75° C. 0.22 ml of tert.-butyl hydrochlorite at one time, and the resulting mixture was stirred for 15 minutes at −75° C. After addition of a solution of 0.2 ml of acetic acid in 2 ml of chloroform, the temperature of the reaction system was elevated to room temperature. The reaction mixture was freed from the solvent by distillation under reduced pressure and the residue was dissolved by adding 20 ml of ethyl acetate and 20 ml of water thereto, and the pH thereof was adjusted to 6.5 with saturated aqueous sodium hydrogen carbonate. The organic layer was separated, and 20 ml of water was added thereto, after which the pH thereof was adjusted to 2.0 with 2 N hydrochloric acid. The organic layer was again separated, washed with 10 ml of water and 10 ml of saturated sodium chloride solution in this order, dried over magnesium sulfate, and freed from the solvent by distillation under reduced pressure. The residue was purified by a column chromatography (stationary phase: silica gel; eluent: a 3:2 mixture of benzene and ethyl acetate) to obtain 0.45 g of diphenylmethyl 7β-[D-α-(2-trichloro ethoxycarbonylamino-4-thiazolyl)-α-(4-ethyl-2,3-dioxo-1-piperazinecarboxamido)-acetamido]-7α-methoxy-3-[5-(1-methyl-1,2,3,4-tetrazolyl)thiomethyl]-Δ$^3$-cephem-4-carboxylate in white powder form, m.p. 155°–177° C. (decomp.), yield 36.4%.

IR (KBr) cm$^{-1}$: νC=O 1785, 1710, 1685. NMR (CDCl$_3$) δvalues: 1.10 (3H, t, —CH$_3$), 3.20–4.30 (10H, m, >CH$_2$×5), 3.41 (3H, s, —CH$_3$), 3.73 (3H, s, —CH$_3$), 4.73, 4.79 (2H, ABq, >CH$_2$), 4.92 (1H, s, >CH), 5.74 (1H, d, >CH), 6.74 (1H, s, >CH), 7.04 (1H, s, >CH), 7.20 (11H, m, —C$_6$H$_5$×2, >NH), 8.34 (1H, bs, >NH), 9.78 (1H, d, >NH).

(3) In 7 ml of 85% formic acid was dissolved 0.4 g of diphenylmethyl 7β-[D-α-(2-trichloroethoxycarbonylamino-4-thiazolyl)-α-(4-ethyl-2,3-dioxo-1-piperazinecarboxamido)-acetamido]-7α-methoxy-3-[5-(1-methyl-1,2,3,4-tetrazolyl)-thiomethyl]-Δ$^3$-cephem-4-carboxylate obtained in (2). To the solution was added 0.4 g of zinc dust with ice-cooling, and the mixture was stirred for 3 hours at the same temperature. The insolubles were removed by filtration and the filtrate was freed from the solvent by distillation under reduced pressure. The residue was dissolved by adding 7 ml of methylene chloride, 3 ml of acetone and 10 ml of water thereto and the pH of the solution was adjusted to 7.0 with saturated aqueous sodium hydrogen carbonate. The organic layer was separated, washed with saturated aqueous sodium chloride solution, dried over magnesium sulfate and freed from the solvent by distillation under reduced pressure to obtain 0.21 g of a white powder. The white powder was dissolved in 2 ml of anisole, and 2 ml of trifluoroacetic acid was added thereto with ice-cooling, after which the solution was stirred at the same temperature for 30 minutes. The insolubles were removed by filtration and the filtrate was freed from the solvent by distillation under reduced pressure. The residue was treated with 5 ml of ethyl acetate to obtain 0.19 g of the trifluoroacetic acid salt of 7β-[D-α-(2-amino-4-thiazolyl)-α-(4-ethyl-2,3-dioxo-1-piperazinecarboxamido)-acetamido]-7α-methoxy-3-[5-(1-methyl-1,2,3,4-tetrazolyl)thiomethyl]-Δ$^3$-cephem-4-carboxylic acid, m.p. 175°–190° C. (decomp.), yield 60.9%.

IR (KBr) cm$^{-1}$: νC=O 1765, 1700, 1675.

In a similar manner, the following compounds were obtained:

Trifluoroacetic acid salt of 7β-[D-α-(2-amino-4-thiazolyl)-α-(4-ethyl-2,3-dioxo-1-piperazinecarboxamido)acetamido]-7α-methoxy-3-[5-(1-carbamoylmethyl-1,2,3,4-tetrazolyl)thiomethyl-Δ$^3$-cephem-4-carboxylic acid.

Trifluoroacetic acid salt of 7β-[D-α-(2-amino-4-thiazolyl)-α-(4-ethyl-2,3-dioxo-1-piperazinecarboxamido)acetamido]-7α-methoxy-3-acetoxymethyl-Δ$^3$-cephem-4-carboxylic acid.

Trifluoroacetic acid salt of 7β-[D-α-(2-amino-4-thiazolyl)-α-(4-ethyl-2,3-dioxo-1-piperazinecarboxamido)acetamido]-7α-methoxy-3-[2-(5-methyl-1,3,4-thiadiazolyl)thiomethyl-Δ$^3$-cephem-4-carboxylic acid.

(4) In 3 ml of hydrous acetone was dissolved 0.16 g of the trifluoroacetic acid salt of 7β-[D-α-(2-amino-4-thiazolyl)-α-(4-ethyl-2,3-dioxo-1-piperazinecarboxamido)acetamido]-7α-methoxy-3-[5-(1-methyl-1,2,3,4-tetrazolyl)thiomethyl]-Δ$^3$-cephem-4-carboxylic acid obtained in (3), and of 0.0197 g (equimolar amount) of pyridine was added, after which the solution was freed from the solvent by distillation under reduced pressure. Water was added to the residue, and the crystals were collected by filtration to obtain 7β-[D-α-(2-amino-4-thiazolyl)-α-(4-ethyl-2,3-dioxo-1-piperazinecarboxamido)-acetamido]-7α-methoxy-3-[5-(1-methyl-1,2,3,4-tetrazolyl)thiomethyl]-Δ$^3$-cephem-4-carboxylic acid.

EXAMPLE 8

(1) To a suspension of 5.0 g of D(—)-alanine in 50 ml of methylene chloride was added 14.9 ml of trimethylchlorosilane. To the mixture was added dropwise at 0° to 5° C. 15.6 ml of triethylamine. The temperature of the resulting mixture was gradually elevated and the reaction was allowed to proceed at 20° C. for 1.5 hours. To the reaction mixture was then added at 5° to 10° C. 20 g of a mixture of 4-ethyl-2,3-dioxo-1-piperazinecarbonyl chloride and triethylamine hydrochloride (in which mixture, 58.02% was the former component). After 2 hours of reaction at 20° C., the reaction mixture was freed from the solvent by distillation. To the residue was added 50 ml of water, and the pH of the mixture was adjusted to 7.5 with sodium hydrogen carbonate, washed with 50 ml of ethyl acetate, and 50 ml of acetonitrile was added thereto, after which the pH thereof was adjusted to 1.5 with 2 N hydrochloric acid. The acetonitrile layer was separated and the aqueous layer was further extracted twice with 50-ml portions of acetonitrile. The acetonitrile layers were washed with saturated aqueous sodium chloride solution and then combined. The combined acetonitrile layer was dried over anhydrous magnesium sulfate and freed from the solvent by distillation under reduced pressure. The residue was recrystallized from n-butanol to obtain 10.8 g of D(—)-α-(4-ethyl-2,3-dioxo-1-piperazinecarboxamido)-propionic acid, m.p. 164°–168° C., yield 75%.

IR (KBr) cm$^{-1}$: νC=O 1710, 1660. NMR (DMSO-d$_6$) δvalues: 1.11 (3H, t, —CH$_3$), 1.39 (3H, d, —CH$_3$), 3.2–4.1 (6H, m, >CH$_2$×3), 4.13 (1H, m, >CH), 9.22 (1H, d, >NH).

(2) To a suspension of 1.5 g of D(—)-α-(4-ethyl-2,3-dioxo-1-piperazinecarboxamido)propionic acid in 15 ml of methylene chloride was added 0.64 ml of 1-methylmorpholine to form a solution. While maintaining the temperature at −15° to −20° C., 0.58 ml of ethyl chlorocarbonate was added to the solution and allowed to react for 1.5 hours. Thereafter, 2.88 g of diphenylmethyl 7β-amino-3-[5-(1-methyl-1,2,3,4-tetrazolyl)thiomethyl)-Δ$^3$-cephem-4-carboxylate was added to the solution and the reaction was allowed to proceed for one hour at −15° to −20° C., and then for 1.5 hours at −10° to 0° C. After removing the solvent by distillation under reduced pressure, 30 ml of water and 30 ml of ethyl acetate were added to the residue and the mixture was stirred thoroughly. The precipitated white crystals were collected by filtration to obtain 4.0 g of diphenylmethyl 7β-[D(−)-α-(4-ethyl-2,3-dioxo-1-piperazinecarboxamido)-propionamido]-3-[5-(1-methyl-1,2,3,4-tetrazolyl)thiomethyl]-Δ³-cephem-4-carboxylate, m.p. 150°-154° C. (decomp.), yield 93.6%.

IR (KBr) cm⁻¹: $\nu C\!=\!\!O$ 1780, 1720, 1680. NMR (CDCl₃) δvalues: 1.08 (3H, t, —CH₃), 1.36 (3H, d, —CH₃), 3.25–4.0 (8H, m, >CH₂×4), 3.8 (3H, s, —CH₃), 4.3 (2H, q, >CH₂), 4.55 (1H, m,⇀CH), 4.99 (1H, d,⇀CH), 5.8 (1H, m,⇀CH), 6.85 (1H, s,⇀CH), 7.2–7.4 (10H, s, —C₆H₅×2), 7.7 (1H, s,⇀CH), 9.3 (1H, s, ×NH).

(3) In a mixture of 20 ml of chloroform and 6 ml of anhydrous tetrahydrofuran was dissolved 1.26 g of diphenylmethyl 7β-[D(−)-α-(4-ethyl-2,3-dioxo-1-piperazinecarboxamido)-propionamido]-3-[5-(1-methyl-1,2,3,4-tetrazolyl)thiomethyl]-Δ³-cephem-4-carboxylate. While maintaining the temperature at −70° C., 2.75 ml of a solution of lithium methoxide (2.184 mmoles/ml) in methanol, was added thereto. The resulting solution was stirred for 3 minutes, and 0.31 ml of tert.-butyl hypochlorite was added and the solution was stirred for 15 minutes at the same temperature. After addition of 0.4 ml of acetic acid, the temperature of the reaction system was elevated to room temperature. The reaction mixture was poured into 30 ml of a citrate buffer solution (pH 7.0). The organic layer was separated, washed with water, and then dried over magnesium sulfate, and freed from the solvent by distillation under reduced pressure. The residue was purified by a column chromatography (stationary phase: silica gel; eluent: a 1:3 mixture of benzene and ethyl acetate) to obtain 0.6 g of diphenylmethyl 7β-[D(−)-α-(4-ethyl-2,3-dioxo-1-piperazinecarboxamido)-propionamido]-7α-methoxy-3-[5-(1-methyl-1,2,3,4-tetrazolyl)thiomethyl]-Δ³-cephem-4-carboxylate, yield 45.8%.

IR (KBr) cm⁻¹: $\nu C\!=\!\!O$ 1770, 1700, 1670. NMR (CDCl₃) δvalues: 1.1 (3H, t, —CH₃), 1.5 (3H, d, —CH₃), 3.5 (3H, s, —CH₃), 3.3–4.2 (8H, m, >CH₂×4), 3.8 (3H, s, —CH₃), 4.35 (2H, q, >CH₂), 4.6 (1H, m,⇀CH), 5.03 (1H, s,⇀CH), 6.88 (1H, s,⇀CH), 7.2–7.4 (10H, s, —C₆H₅×2), 8.0 (1H, s, >NH), 9.25 (1H, d, >NH).

(4) In 8 ml of anisole was dissolved 1.2 g of diphenylmethyl 7β-[D(−)-α-(4-ethyl-2,3-dioxo-1-piperazinecarboxamido)-propionamido]-7α-methoxy-3-[5-(1-methyl-1,2,3,4-tetrazolyl)thiomethyl]-Δ³-cephem-4-carboxylate, and 5 ml of trifluoroacetic acid was added to the solution with ice-cooling. The solution was stirred at the same temperature for 30 minutes. After completion of the reaction, the solvent was removed by distillation under reduced pressure. The residue was dissolved by adding 30 ml of ethyl acetate and 30 ml of water and the pH of the solution was adjusted to 7.0 with aqueous sodium hydrogen carbonate solution. The aqueous layer was separated, and 30 ml of acetonitrile was added thereto, after which the pH thereof was adjusted to 2.0 with 2 N hydrochloric acid. The acetonitrile layer was separated and the aqueous layer was extracted twice with 30-ml portions of acetonitrile. The extract acetonitrile layers were washed with saturated aqueous sodium chloride solution and then combined with the above acetonitrile layer. The combined acetonitrile layer was dried over anhydrous magnesium sulfate and freed from the solvent by distillation under reduced pressure to obtain 0.5 g of 7β-[D(−)-α-(4-ethyl-2,3-dioxo-1-piperazinecarboxamido)-propionamido]-7α-methoxy-3-[5-(1-methyl-1,2,3,4-tetrazolyl)thiomethyl]-Δ³-cephem-4-carboxylic acid, m.p. 165° C. (decomp.), yield 53.2%.

IR (KBr) cm⁻¹: $\nu C\!=\!\!O$ 1770, 1705, 1670, 1650. NMR (DMSO-d₆) δvalues: 1.12 (3H, t, —CH₃), 1.40 (3H, d, —CH₃), 3.44 (3H, s, —CH₃), 3.4–4.2 (8H, m, >CH₂×4), 3.99 (3H, s, —CH₃), 4.3 (2H, q, >CH₂), 4.5 (1H, m, CH), 5.1 (1H, s, CH), 9.13 (1H, d, >NH), 9.40 (1H, s, >NH).

In a similar manner, the following compounds were obtained:

7β-[DL-α-(4-ethyl-2,3-dioxo-1-piperazinecarboxamido)-α-(chloromethyl)-acetamido]-7α-methoxy-3-[5-(1-methyl-1,2,3,4-tetrazolyl)thiomethyl]-Δ³-cephem-4-carboxylic acid, m.p. 143°-146° C. (decomp.).

IR (KBr) cm⁻¹: $\nu C\!=\!\!O$ 1775, 1730-1650. NMR (DMSO-d₆) δvalues: 1.15 (3H, t, —CH₃), 3.45 (3H, s, —OCH₃), 3.97 (3H, s, —CH₃), 3.30–4.10 (10H, m, >CH₂×5), 4.30 (2H, bs, >CH₂), 4.95 (1H, m, CH), 5.05 (1H, s, CH), 9.45 (1H, d, >NH), 9.60 (1H, s, >NH).

7β-[DL-α-(4-ethyl-2,3-dioxo-1-piperazinecarboxamido)-α-(hydroxymethyl)-acetamido]-7α-methoxy-3-[5-(1-methyl-1,2,3,4-tetrazolyl)thiomethyl]-Δ³-cephem-4-carboxylic acid, m.p. 108°-110° C. (decomp.).

IR (KBr) cm⁻¹: $\nu C\!=\!\!O$ 1765, 1720-1650.

7β-[DL-α-(2,3-dioxo-1-piperazinecarboxamido)-propanionamido]-7α-methoxy-3-[5-(1-methyl-1,2,3,4-tetrazolyl)thiomethyl]-Δ³-cephem-4-carboxylic acid.

EXAMPLE 9

In the same manner as in Example 1, the following compounds were produced:

7β-[D(−)-α-(2,3-dioxo-1-piperazinecarboxamido)-α-(2-thienyl)-acetamido]-7α-methoxy-3-[5-(1-methyl-1,2,3,4-tetrazolyl)thiomethyl]-Δ³-cephem-4-carboxylic acid.

7β-[D(−)-α-(2,3-dioxo-1-piperazinecarboxamido)-α-(2-thienyl)-acetamido]-7α-methoxy-3-acetoxymethyl-Δ³-cephem-4-carboxylic acid.

What is claimed is:

1. A 7α-methoxy-cephalosporin or a salt thereof, said 7α-methoxy-cephalosporin being represented by the formula

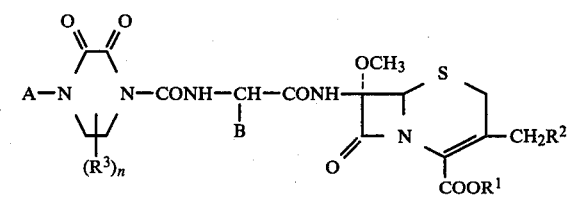

wherein R¹ represents a hydrogen atom or a carboxyl-protecting group; R² represents a substituted or unsubstituted lower alkoxy, lower alkylthio, or $C_{1-10}$ acyloxy group, the substituent of the substituted group being selected from halogen, lower alkyl, phenyl, $C_{2-5}$ alkenyl, hydroxyl, lower alkoxy, lower alkylthio, nitro, cyano, lower alkylamino, di-lower alkylamino, $C_{1-10}$ acylamino, $C_{1-10}$ acyl, $C_{1-10}$ acyloxy, $C_{1-10}$ acyl-lower alkyl, carboxyl, carbamoyl, amino-lower alkyl, N-lower alkylamino-lower alkyl, N,N-di-lower alkylamino-lower alkyl, hydroxy-lower alkyl, hydroxyimino-lower alkyl, lower alkoxy-lower alkyl, carboxyl-lower alkyl, sulfo-lower alkyl, sulfo, sulfamoyl-lower alkyl, sulfamoyl, carbamoyl-lower alkyl, carbamoyl-$C_{2-5}$ alkenyl, and N-hydroxycarbamoyl-lower alkyl; R³ represents a lower alkyl group; n is 0, 1 or 2; A represents a hydrogen atom or a substituted or unsubstituted straight or branched chain $C_{1-14}$ alkyl group, the substituent of the substituted group being selected from halogen, lower alkoxy, cyano, nitro, carboxyl, lower alkoxycarbonyl, lower alkylthio, and $C_{1-10}$ acyl; and B represents a substituted or unsubstituted $C_{5-6}$ cycloalkyl, $C_{5-6}$ cycloalkenyl, $C_{5-6}$ cycloalkadienyl or heterocyclic group, said heterocyclic group being composed of a 5 or 6 membered aromatic heterocyclic ring which is composed of carbon and at least one hetero atom selected from S, O and N, or of said aromatic heterocyclic ring fused to a benzene ring, the substituent of the substituted group being selected from halogen, lower alkyl, lower alkoxy, hydroxyl, $C_{1-10}$ acyl, $C_{1-10}$ acyloxy, mercapto, lower alkylthio, nitro, amino, protected amino, imino, protected imino, and carboxyl.

2. A 7α-methoxycephalosporin or a salt thereof according to claim 1, wherein B represents a heterocyclic group.

3. A 7α-methoxycephalosporin or a salt thereof according to claim 2, wherein B represents a thienyl group.

4. A 7α-methoxycephalosporin or a salt thereof according to claim 3, wherein A represents a lower alkyl group and n is 0.

5. A 7α-methoxycephalosporin or a salt thereof according to claim 4, wherein B represents a 2-thienyl group.

6. A 7α-methoxycephalosporin or a salt thereof according to claim 3 or 4, wherein $R^2$ represents an acetoxy group.

7. A 7α-methoxycephalosporin or a salt thereof according to claim 2, wherein B represents a furyl group.

8. A 7α-methoxycephalosporin or a salt thereof at its acidic group according to claim 7, wherein A represents a lower alkyl group and n is 0.

9. A 7α-methoxycephalosporin or a salt thereof according to claim 7 or 8, wherein $R^2$ represents an acetoxy group.

10. A 7α-methoxycephalosporin or a salt thereof according to claim 2, wherein B represents

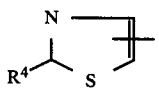

or its tautomer,

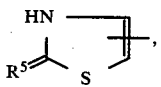

where $R^4$ represents an amino group or protected amino group and $R^5$ represents an imino group or protected imino group.

11. A 7α-methoxycephalosporin or a salt thereof according to claim 10, wherein A represents a lower alkyl group and n is 0.

12. A 7α-methoxycephalosporin or a salt thereof according to claim 10 or 11, wherein $R^2$ represents an acetoxy group.

13. A 7α-methoxycephalosporin or a salt thereof according to claim 1, wherein B represents 1,4-cyclohexadienyl group.

14. A 7α-methoxycephalosporin or a salt thereof at its acidic group according to claim 13, wherein A represents a lower alkyl group and n is 0.

15. A 7α-methoxycephalosporin or a salt thereof according to claim 13 or 14, wherein $R^2$ represents an acetoxy group.

16. A 7α-methoxycephalosporin or a salt thereof according to claim 1, wherein A represents a lower alkyl group, n is 0, B represents a thienyl, furyl or 2-aminothiazolyl group, and $R^2$ represents an acetoxy group.

17. A 7α-methoxycephalosporin or a pharmaceutically acceptable salt thereof according to claim 16, wherein A represents ethyl group and B represents 2-thienyl group.

18. A 7α-methoxycephalosporin or a salt thereof according to claim 1, wherein A represents a hydrogen atom, n is 0, B represents a thienyl, furyl or 2-aminothiazolyl group, and $R^2$ represents an acetoxy group.

19. A pharmaceutical composition useful for treating bacterial infections in humans and mammals which comprises an antibacterially effective amount of a compound or its pharmaceutically acceptable salt as claimed in claim 1, in combination with a pharmaceutically acceptable inert diluent or carrier.

20. 7β-[D(−)-α-(4-ethyl-2,3-dioxo-1-piperazinecarboxamido)-α-(2-thienyl)-acetamido]-7α-methoxy-3-acetoxymethyl-Δ³-cephem-4-carboxylic acid, or a pharmaceutically acceptable salt thereof.

21. 7β-[D(−)-α-(4-ethyl-2,3-dioxo-1-piperazinecarboxamido)-α-(1,4-cyclohexadienyl)-acetamido]-7α-methoxy-3-acetoxymethyl-Δ³-cephem-4-carboxylic acid, or a pharmaceutically acceptable salt thereof.

22. 7β-[D-α-(2-amino-4-thiazolyl)-α-(4-ethyl-2,3-dioxo-1-piperazinecarboxamido)-acetamido]-7α-methoxy-3-acetoxymethyl-Δ³-cephem-4-carboxylic acid, or a pharmaceutically acceptable salt thereof.

23. 7β-[D(−)-α-(2,3-dioxo-1-piperazinecarboxamido)-α-(2-thienyl)-acetamido]-7α-methoxy-3-acetoxymethyl-Δ³-cephen-4-carboxylic acid, or a pharmaceutically acceptable salt thereof.

* * * * *